United States Patent [19]

Tai et al.

[11] Patent Number: 4,833,264

[45] Date of Patent: May 23, 1989

[54] 5- OR 6-ALKOXYCARBONYL-2,3-DICYANONAPH-THALENES

[75] Inventors: Seiji Tai; Shigeru Hayashida; Nobuyuki Hayashi, all of Hitachi, Japan

[73] Assignee: Hitachi Chemical Co., Ltd., Tokyo, Japan

[21] Appl. No.: 172,290

[22] Filed: Mar. 23, 1988

[30] Foreign Application Priority Data

Mar. 23, 1987 [JP] Japan .................................. 62-68316

[51] Int. Cl.$^4$ ............................................. C07C 69/80

[52] U.S. Cl. .................................................... 558/416
[58] Field of Search ........................................ 558/416

[56] References Cited

U.S. PATENT DOCUMENTS 4,740,620  4/1988  Dixon et al. ......................... 558/416

Primary Examiner—Mary C. Lee
Assistant Examiner—J. Richter
Attorney, Agent, or Firm—Antonelli, Terry & Wands

[57] ABSTRACT

A 5- or 6-alkoxycarbonyl-2,3-dicyanonaphthalene is a useful intermediate for synthesizing a tetrakis(alkoxycarbonyl) metal naphthalocyanine.

9 Claims, 46 Drawing Sheets

5- OR 6-ALKOXYCARBONYL-2,3-DICYANONAPHTHALENES

BACKGROUND OF THE INVENTION

This invention relates to a 5- or 6-alkoxycarbonyl-2,3-dicyanonaphthalene which is useful as an intermediate for synthesis of a tetrakis(alkoxycarbonyl) metal naphthalocyanine, and a process for production thereof.

In recent years, various attempts have been made to use diode laser as a light source, for example, in laser beam printers using an electrophotographic plate and laser beam as a light source. In this case, the wavelength of said light source is about 800 nm, and therefore there is eagerly desired an electrophotographic plate having an organic charge generating material which absorbs near infrared rays near 800 nm.

As organic dyes which absorb near infrared rays cyanine dyes have heretofore been well known, and metal complexes of oximes and thiols and aminated guinone derivatives and also known as dyes which absorb near infrared rays [Yuki Gosei Kagaku Kyokai Shi, vol. 43, p.334 (1985), Shikizai Kyokai Shi, vol. 53, p.197 (1980), and Shikizai Kyokai Shi, vol. 58, p.220 (1985)].

However, the cyanine dyes have a very low stability against light and hence their employement has many restrictions. The metal complexes of oximes and thiols are disadvantageous in that the metals are released from the complexes in a certain medium, resulting in loss of the ability to absorb near infrared rays. The aminated quinone derivatives are very poor in ability to absorb near infrared rays.

On the other hand, as sensitive plates which have a high stability against light and are sensitive in the vicinity of 800 nm, there have been reported those endowed with long-wavelength sensitivity by forming as charge generating material layer a thin film of metallophthalocyanine having a metal in group III or IV of the periodic table as central metal by vacuum evaporation, then immersing the thin film in a shifting agent solution or bringing the same into contact with vapor of the solution, and thereby shifting the inherent absorption band near 700 nm to about 800 nm (Japanese Patent Application Kokai (Laid-Open) Nos. 61-45249 and 60-260054). However, in this case, the metal phthalocyanine thin film having a metal in group III or IV in the periodic table as central metal which is used as a charge generating material layer involves the following serious problem. The thin film has essentially no absorption in the vicinity of 800 nm, and unless treated with a shifting agent, a sensitive plate formed by use of the thin film has no or low sensitivity to light near 800 nm (see Japanese Patent Application Kokai (Laid-Open) No. 58-158649).

SUMMARY OF THE INVENTION

An object of this invention is to provide a synthesis intermediate for obtaining a naphthalocyanine derivative free from the above problem in dyes which absorb near infrared rays, namely a naphthalocyanine derivative which is very excellent in ability to absorb near infrared rays by virtue of substitution in the naphthalene ring by an alkoxycarbonyl group, or also in ability to absorb visible rays when the central metal is properly selected, and moreover which is excellent in solubility in various organic solvents; and a process for production thereof.

This invention provides a 5- or 6-alkoxycarbonyl-2,3-dicyanonaphthalene represented by the formula:

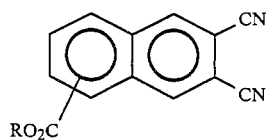

(I)

wherein R is an alkyl group having 1 to 22 carbon atoms.

This invention further provides a process for synthesizing a 5- or 6-alkoxycarbonyl-2,3-dicyanonaphthalene of the formula (I) which comprises irradiating with light, with heating, an alkyl 2,3- or 3,4-dimethylbenzoate of the formula:

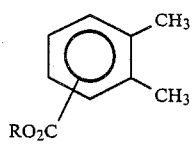

(II)

wherein R is an alkyl group having 1 to 22 carbon atoms, and a N-bromosuccinimide of the formula:

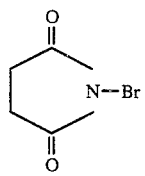

(III)

to obtain a compound of the formula:

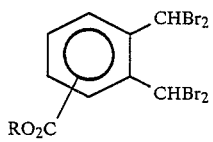

(IV)

wherein R is an alkyl group having 1 to 22 carbon atoms, and reacting this compound with fumaronitrile of the formula:

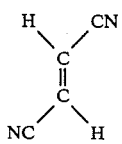

(V)

with heating.

This invention further provides a process for synthesizing a 5- or 6-alkoxycarbonyl-2,3-dicyanonaphthalene of the formula:

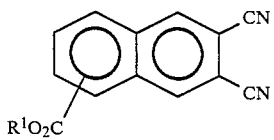

(I')

wherein $R^1$ is an alkyl group having 1 to 22 carbon atoms which is different from R which comprises reacting a 5- or 6- alkoxycarbonyl-2,3-dicyanonaphthalene of the formula:

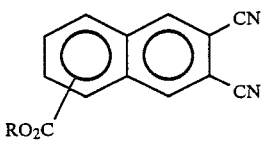

wherein R is an alkyl group having 1 to 22 carbon atoms, the above process with an alcohol of the formula:

$$R^1OH \qquad (VI)$$

wherein $R^1$ is as defined above, with heating.

DESCRIPTION OF THE PREFERRED EMBODIMENTS

Figure 1:
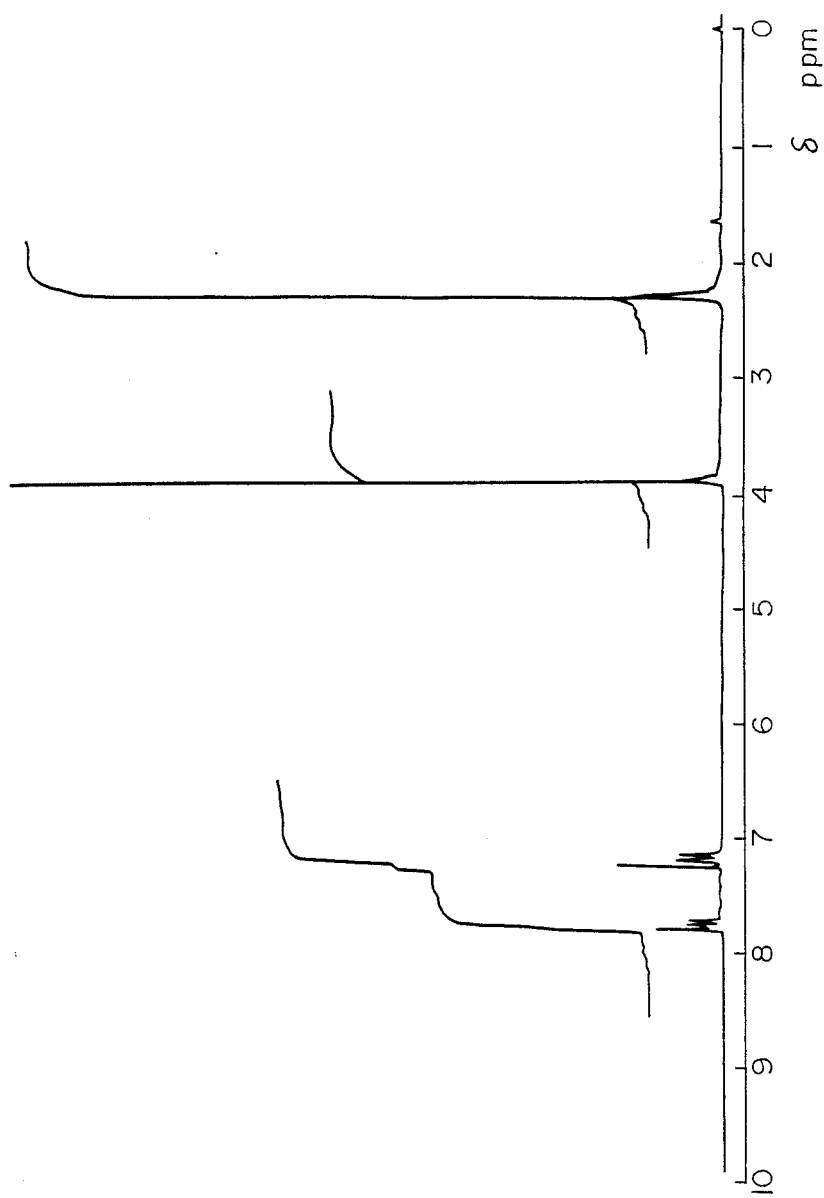
FIG. 1 is an NMR spectrum of methyl 3,4-dimethylbenzoate.

By reacting a 5- or 6-alkoxycarbonyl-2,3-dicyanonaphthalene of the formula:

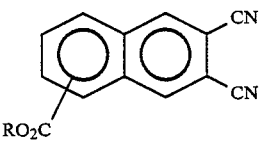

wherein R is an alkyl group having 1 to 22 carbon atoms, with a metal or a metal salt, there can be synthesized in high yield a tetrakis(alkoxycarbonyl) metal naphthalocyanine which is soluble in aromatic and halogenated solvents and can be easily purified to be improved in purity.

As the aromatic solvents, there can be used benzene, toluene, xylene, chlorobenzene, dichlorobenzene, 1,2,4-trimethylbenzene, 1,2,3-trimethylbenzene, 1- chloronaphthalene, 1-bromonaphthalene, quinoline, etc. As the halogenated solvents, there can be used methylene chloride, chloroform, carbon tetrachloride, trichloroethane, etc.

The 5- or 6-(alkoxycarbonyl)-2,3-dicyanonaphthalene of the formula (I) can be synthesized by irradiating, under reflux, an alkyl 2,3- or 3,4-dimethylbenzoate of the formula:

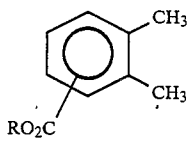
(II)

wherein R is an alkyl group having 1 to 22 carbon atoms, and N-bromosuccinimide of the formula:

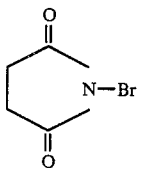
(III)

to obtain a compound of the formula:

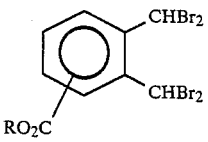
(IV)

wherein R is an alkyl group having 1 to 22 carbon atoms, and reacting this compound with fumaronitrile of the formula:

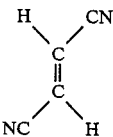
(V)

with heating.

The reaction of the alkyl 2,3- or 3,4-dimethylbenzoate of the formula (II) with N-bromosuccinimide of the formula (III) can be carried out by refluxing 0.2 mol of the alkyl 2,3- or 3,4-dimethylbenzoate and 0.8 mol of N-bromosuccinimide with heating for 4 to 12 hours under irradiation from a high pressure mercury arc lamp in a solvent which is inert toward the irradiation. The reaction requires addition of a peroxide capable of generating a radical, as a reaction initiator. The peroxide includes benzoyl peroxide, octanoyl peroxide, cyclohexanone peroxide, isobutyryl peroxide, 2,4-dichlorobenzoyl peroxide, methyl ethyl ketone peroxide, etc. The peroxide is used usually in an amount of 500 mg to 2 g per 500 ml of the solvent. The solvent inert to the irradiation is properly selected from halogenated solvents such as chloroform, carbon tetrachloride and the like, or aromatic solvents such as benzene, chlorobenzene and the like.

The next reaction of the compound of the formula (IV) with fumaronitrile of the formula (V) can be carried out by placing fumaronitrile of the formula (V) together with the compound of the formula (IV) in an amount of 1 to 2 mols per mol of the latter. The reaction temperature is preferably 70° to 100° C., and the reaction time is preferably 5 to 10 hours. As the solvent, polar organic solvents such as N,N-dimethylformamide, N,N-dimethylacetamide, dimethyl sulfoxide, N,N-diethylformamide, N,N-diethylacetamide, and the like are preferred The alkyl 2,3- or 3,4-dimethylbenzoate of the formula (II) can be produced by the pathway of the formula:

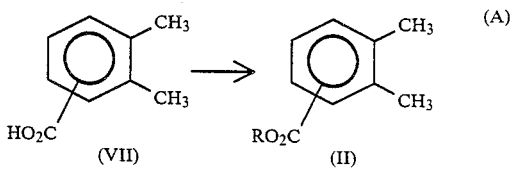
(A)

In detail, an alcohol [ROH, wherein R is an alkyl group having 1 to 22 carbon atoms] is placed together with 2,3- or 3,4-dimethylbenzoic acid [the formula (VII)] in an amount of 1 mol or more per mol of the latter, and dehydration is carried out by heating in the presence or absence of a solvent in the presence of a Lewis acid as catalyst in an amount of 25 to 50 mol % of the amount of 2,3- or 3,4-dimethylbenzoic acid used, whereby the alkyl 2,3- or 3,4-dimethylbenzoate [the formula (II)] can be obtained. As the solvent, benzene, toluene, xylene, chlorobenzene, dichlorobenzene, trimethylbenzene, 1-chloronaphthalene, etc. are preferred. As the catalyst, sulfuric acid, p-toluenesulfonic acid, benzenesulfonic acid, etc. are preferred. The reaction temperature is preferably 80° to 240° C., and the reaction time is preferably 1 to 10 hours.

By placing an alcohol of the formula (VI) together with one 5- or 6-alkoxycarbonyl-2,3-dicyanonaphthalene of the formula (I) (wherein R is an alkyl group having 1 to 22 carbon atoms) in an amount of 1 mol or more per mol of the latter and carrying out transesterification reaction by refluxing them with heating in the presence or absence of a solvent in the presence of a Lewis acid as catalyst in an amount equimolar with the starting 5- or 6-alkoxycarbonyl-2,3-dicyanonaphthalene, or a larger amount, another 5- or 6-alkoxycarbonyl-2,3-dicyanonaphthalene can be obtained. As the solvent, benzene, toluene, xylene, chlorobenzene, dichlorobenzene, trimethylbenzene, 1-chloronaphthalene, etc. are preferred. As the catalyst, sulfuric acid, p-toluenesulfonic acid, benzenesulfonic acid, etc. are preferred. The reaction temperature is preferably 80° to 240° C., and the reaction time is preferably 1 to 50 hours.

The 5- or 6-alkoxycarbonyl-2,3-dicyanonaphthalene of the formula () (wherein R is an alkyl group having 1 to 22 carbon atoms) can be isolated and purified from the reaction mixture by extraction of the reaction mixture with chloroform, followed by recrystallization, column chromatography, etc.

A tetrakis(alkoxycarbonyl) metal naphthalocyanine can be obtained by placing the above-mentioned metal or metal salt together with the 5- or 6-alkoxycarbonyl-2,3-dicyanonaphthalene of the formula (I) in an amount of 0.1 to 1 mol per mol of the latter, and reacting them with each other with heating. In this case, the reaction temperature is preferably 150° to 300° C., and the reaction time is preferably 30 minutes to 10 hours. For these conditions, it is preferable to carry out the reaction without any solvent or by use of a solvent such as urea, tetralin, quinoline, 1-chloronaphthalene, 1-bromonaphthalene, 1,2,4-trimethylbenzene, 1,2,3-trimethylbenzene, dichlorobenzene, trichlorobenzene, or the like. The metal or metal salt includes Mg, Zn, AlCl$_3$, InCl$_3$, SiCl$_4$, GeCl$_4$, SnCl$_2$, PbCl$_2$, TiCl$_4$, VCl$_3$, CrCl$_3$, MoCl$_2$, Mn(O.COCH$_3$)$_2$, FeCl$_3$, CoCl$_2$, NiCl$_2$, PtCl$_2$, PdCl$_2$, etc.

The tetrakis(alkoxycarbonyl) metal naphthalocyanine can be isolated and purified from the reaction mixture, for example, by washing the reaction mixture with diluted hydrochloric acid, thereafter washing the same sufficiently with a poor solvent for the naphthalocyanine, such as water, alcohol, acetone, or the like, concentrating a substance soluble in a halogenated or aromatic solvent to dryness, and collecting the resulting solid.

The tetrakis(alkoxycarbonyl) metal naphthalocyanine is represented by the formula:

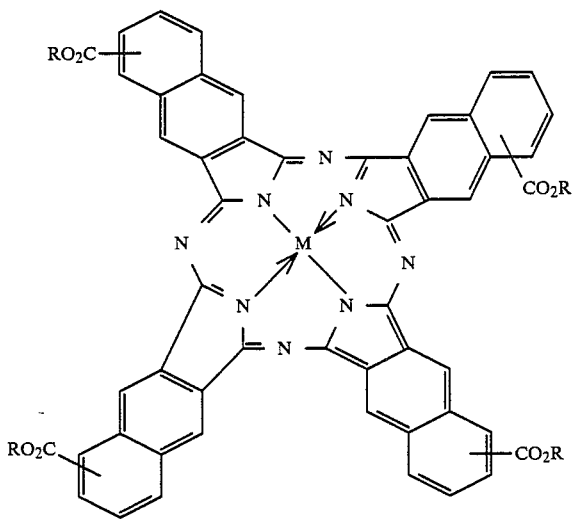

wherein four R's, which may be the same or different, are alkyl groups having 1 to 22 carbon atoms; and M is one member selected from the group consisting of metals in group Ib such as Cu, etc., metals in group IIa such as Mg, etc., metals in group IIb such as Zn, etc.; metals in group IIIa or halides or hydroxides thereof such as Al, ClAl, HOAl, In, ClIn, etc., metals in groups IVa or halides or hydroxides thereof such as Si, Cl$_2$Si, (HO)$_2$Si, Ge, Cl$_2$Ge, (HO)$_2$Ge, Sn, Cl$_2$Sn, (HO)$_2$Sn, Pb, etc., metals in group IVb or oxides thereof such as Ti, OTi, etc., oxides of metals in group Vb such as OV, etc., metals in group VIb such as Cr, Mo, etc., metals in group VIIb or halides thereof such as Mn, ClMn, etc., or metals in group VIII or halides thereof such as Fe, ClFe, Co, Ni, Pt, Pd, etc.

The tetrakis(alkoxycarbonyl) metal naphthalocyanine is useful as an electrophotographic photosensitive material (a charge generating material) for electrophotographic plate. Production of an electrophotographic plate by use of the naphthalocyanine as electrophotographic photosensitive material is conducted as follows.

A monolayer of a mixture of the tetrakis(alkoxycarbonyl) metal naphthalocyanine and a charge transport material can be formed as photoconductive layer on an electroconductive layer. It is also possible to form a so-called double layer structure as photoconductive layer on an electroconductive layer by forming separate layers of a charge generating material and a charge transport material, respectively.

When the monolayer structure is employed, the proportion of the charge transport material to said charge generating material is usually 1 to 50 parts by weight of the former to 1 part by weight of the latter. The total thickness of the photoconductive layer is adjusted usually to 5 to 100 μm. On the other hand, when the double layer structure is employed, the thickness of the charge generating material layer is adjusted usually to 0.1 to 5 μm and that of the charge transport material layer to 5 to 30 μm. However, in either case, it is desirable to determine the thickness(es) finally with caution so as not to impair the photosensitivity, i.e., the charge accepting characteristics. When the thickness of the photoconductive layer is too large the flexibility of the layer itself tends to be lowered, and therefore care must be taken.

The charge transport material includes pyrazoline derivatives, hydrazone derivatives, triphenylmethane derivatives, oxadiazole derivatives, oxazole derivatives, carbozole derivatives, stilbene derivatives, etc. A known binder can be used in the photoconductive layer. The binder is selected from the group consisting of linear saturated polyester resins, polycarbonate resins, acrylic resins, butyrol resins, polyketone resins, polyurethane resins, poly-N-vinylcarbazole, poly-(p-vinylphenyl)anthracene, etc. The using amount of the binder is preferably 1 to 50 parts by weight per part by weight of the charge generating material in the case of a photoconductor having the monolayer structure. In the case of a photoconductor having a double layer structure, the binder should be incorporated, at least, into a layer made of the charge transport material preferably in an amount of 1 to 50 parts by weight per part by weight of the charge transport material. In the electroconductive layer, aluminum, brass, copper, gold etc. can be used.

This invention is explained below with reference to Examples, which are not by way of limitation but by way of illustration.

SYNTHESIS EXAMPLE 1

[Synthesis of methyl 3,4-dimethylbenzoate]

To 200 ml of methanol was added 47.6 g (0.317 mol) of 3,4-dimethylbenzoic acid, and the resulting mixture was refluxed for about 4 hours in the presence of about 6 ml of concentrated sulfuric acid with continuous extraction of water by use of Molecular Sieves 3A (a drying agent mfd. by Wako Pure Chemical Industries, Ltd.). After the mixture was allowed to cool, about 600 ml of water was added and the resulting mixture was extracted three times with about 200 ml of benzene. The benzene solution thus obtained was washed three times with a saturated aqueous sodium hydrogencarbonate solution and then three times with water, and subsequently dried by addition of anhydrous sodium sulfate. The benzene solution was concentrated and then distilled under reduced pressure to obtain 49.4 g of a colorless liquid at a boiling point of 133°–134° C./30 mm Hg. This liquid was identified as methyl 3,4-dimethylbenzoate from the following analysis results:

| | (1) Elementary analysis values: | |
|---|---|---|
| | C | H |
| Calculated (%) | 73.15 | 7.37 |
| Found (%) | 73.13 | 7.46 |

(2) Nuclear magnetic resonance (NMR) spectrum values (the NMR spectrum is shown in FIG. 1): $CDCl_3$ solvent: δ values 7.81 (1H, br-s), 7.76 (1H, dd, J=7.93, 1.53 Hz), 7.18 (1H, d, J=7.93 Hz), 3.89 (3H, s), 2.30 (6H, s).

Figure 2:
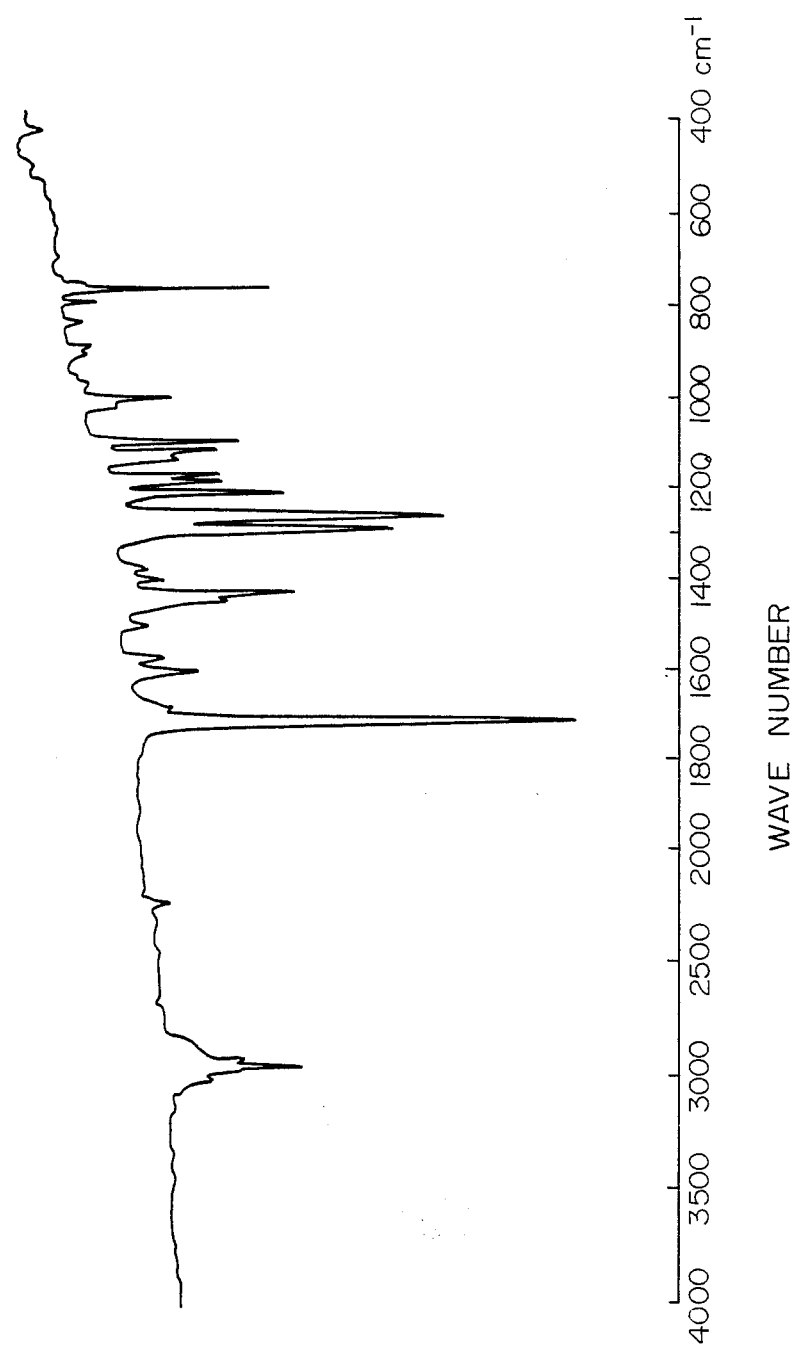
FIG. 2 is an IR spectrum of methyl 3,4-dimethylbenzoate.

(3) Infrared absorption (IR) spectrum (neat) is shown in FIG. 2. The spectrum shows an absorption due to ester C=O stretching vibration near 1710 $cm^{-1}$.

SYNTHESIS EXAMPLE 2

[Synthesis of n-amyl 3,4-dimethylbenzoate]

To 150 ml of benzene was added 60 g (0.4 mol) of 3,4-dimethylbenzoic acid, 43 ml (0.4 mol) of n-amyl alcohol and 22 g (0.116 mol) of p-toluenesulfonic acid monohydrate, and the resulting mixture was refluxed for 3 hours while being dehydrated by use of a Dean-Stark trap and then Molecular Sieves 3A. After cooling, the reaction mixture was washed three times with 100 ml of a saturated aqueous sodium hydrogencarbonate solution and then three times with water. The benzene solution thus obtained from the reaction mixture was then dried over anhydrous magnesium sulfate and concentrated under reduced pressure. The oily substance thus obtained was distilled under reduced pressure to obtain 77 g of a colorless liquid at 145°–148° C./8 mm Hg. This liquid was identified as n-amyl 3,4-dimethylbenzoate from the following analysis results:

| | (1) Elementary analysis values: | |
|---|---|---|
| | C | H |
| Calculated (%) | 76.33 | 9.15 |
| Found (%) | 76.22 | 9.25 |

Figure 3:
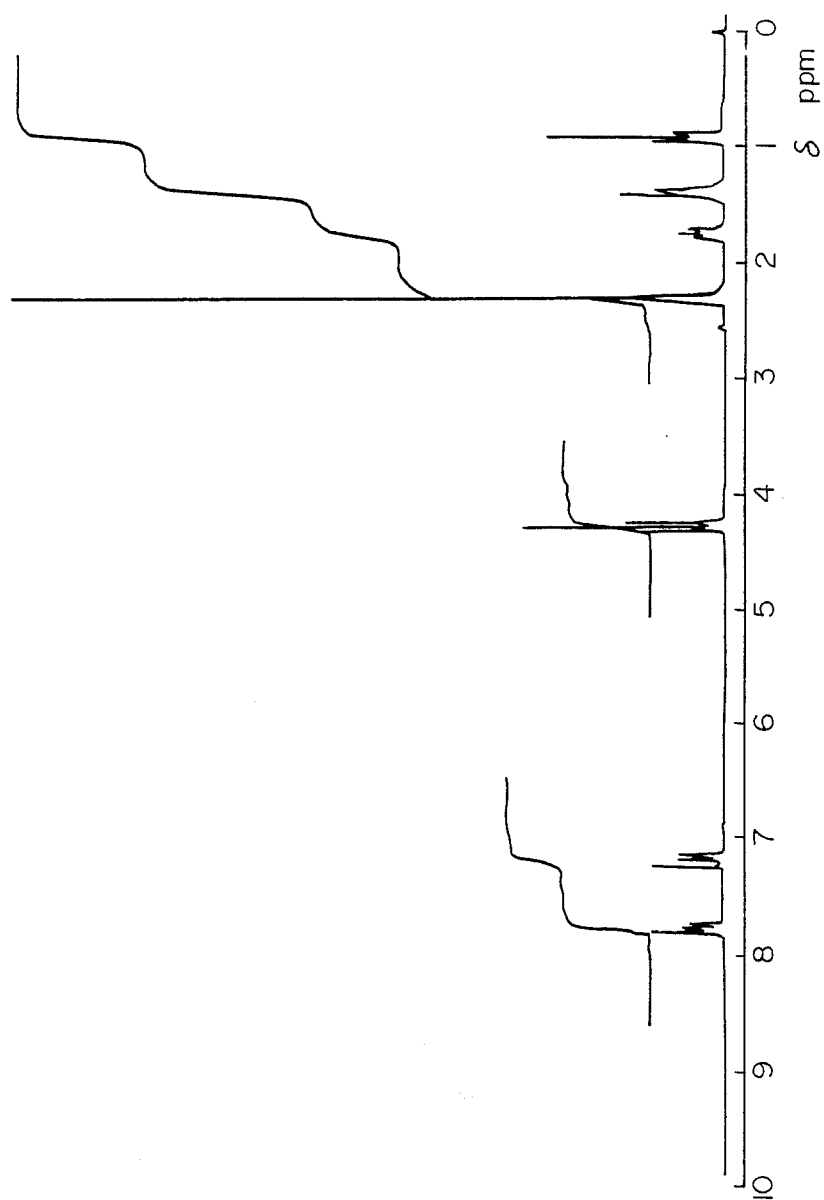
FIG. 3 is an NMR spectrum of n-amyl 3,4-dimethylbenzoate.

(2) NMR spectrum values (the NMR spectrum is shown in FIG. 3): $CDCl_3$ solvent: δ values 7.81 (1H, br-s), 7.77 (1H, dd, J=7.94, 1.98 Hz), 7.18 (1H, d, J=7.94 Hz), 4.29 (2H, t, J=6.72 Hz), 2.30 (6H, s), 1.76 (2H, quintet, J=6.72 Hz), 1.40 (4H, m), 0.93 (3H, t, J=6.72 Hz).

Figure 4:
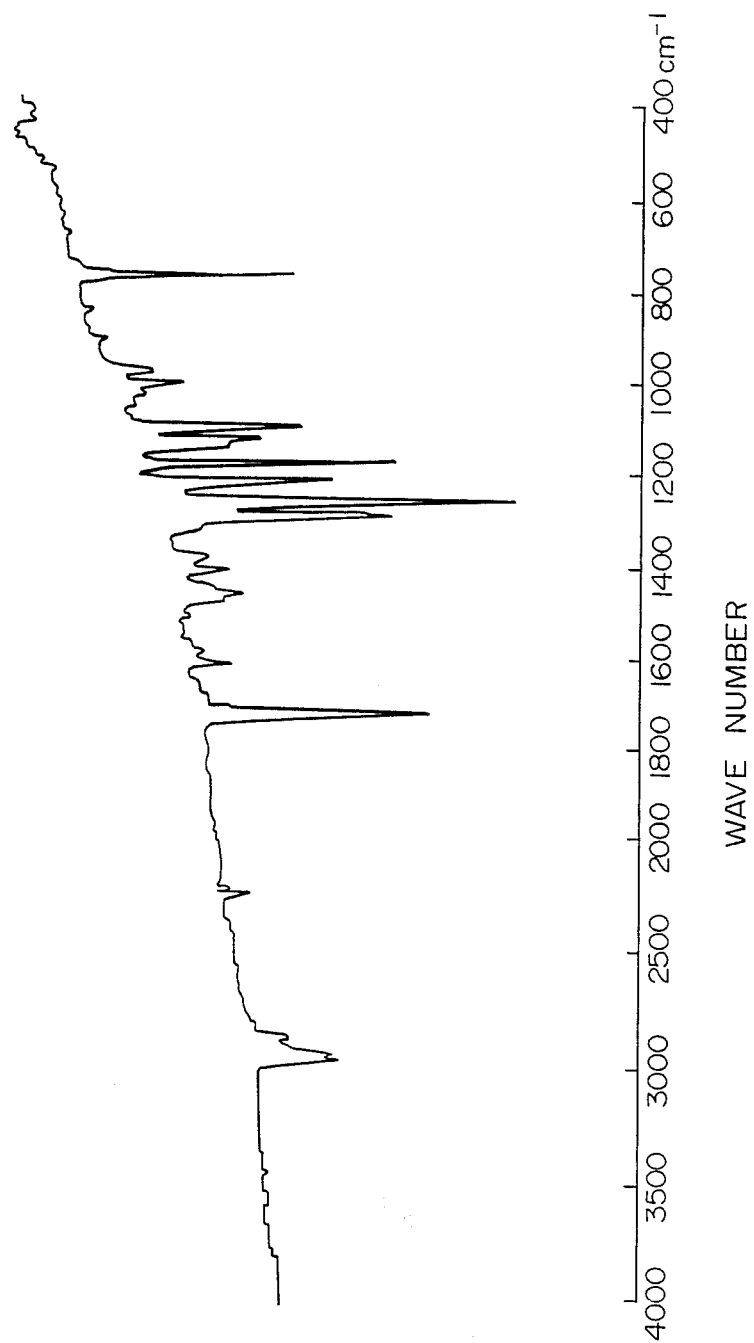
FIG. 4 is an IR spectrum of n-amyl 3,4-dimethylbenzoate.

(3) IR spectrum (neat) is shown in FIG. 4. The spectrum shows an absorption due to ester C=O stretching vibration near 1710 $cm^{-1}$.

SYNTHESIS EXAMPLE 3

[Synthesis of n-octyl 3,4-dimethylbenzoate]

To 100 ml of benzene were added 40 g (0.27 mol) of 3,4-dimethylbenzoic acid, 100 ml (0.635 mol) of n-octanol and 22 g (0.116 mol) of p-toluenesulfonic acid monohydrate, and the resulting mixture was refluxed for about 6 hours while being dehydrated by use of a Dean-Stark trap and then Molecular Sieves 3A. After cooling, the reaction mixture was treated in the same manner as in Synthesis Example 2 and distilled under reduced pressure to obtain 60.5 g of a colorless liquid at a boiling point of 148°–152° C./3 mm Hg. This liquid was identified as n-octyl 3,4-dimethylbenzoate from the following analysis results:

| | (1) Elementary analysis values: | |
|---|---|---|
| | C | H |
| Calculated (%) | 77.82 | 9.99 |
| Found (%) | 77.21 | 10.07 |

Figure 5:
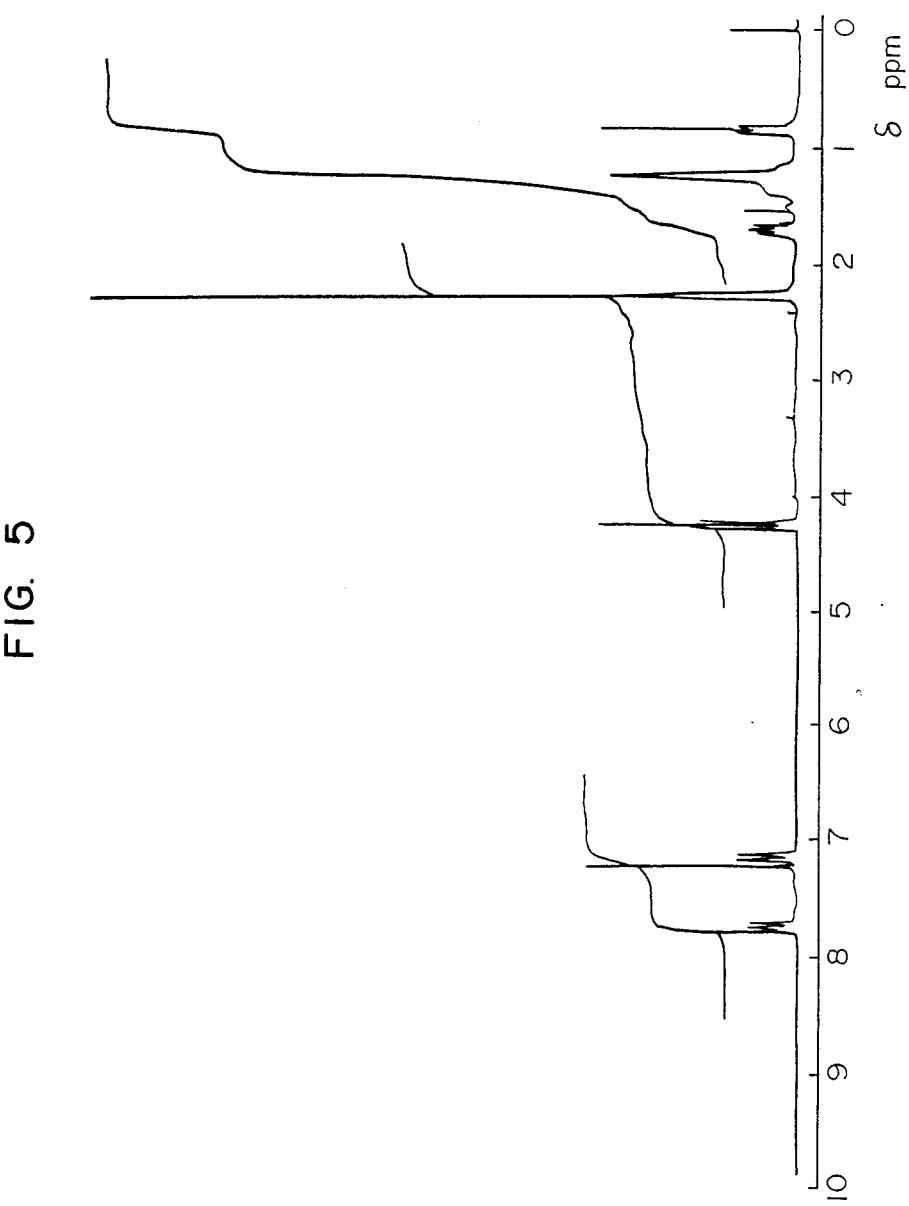
FIG. 5 is an NMR spectrum of n-octyl 3,4-dimethylbenzoate.

(2) NMR spectrum values (the NMR spectrum is shown in FIG. 5): $CDCl_3$ solvent: δ values 7.81 (1H, br-s), 7.77 (1H, dd, J=7.63, 1.83 Hz), 7.19 (1H, d, J=7.63 Hz), 4.29 (2H, t, J=6.72 Hz), 2.31 (6H, s), 1.76 (2H, quintet, J=6.72 Hz), 1.1–1.5 (10H, m), 0.88 (3H, t, J=6.72 Hz).

Figure 6:
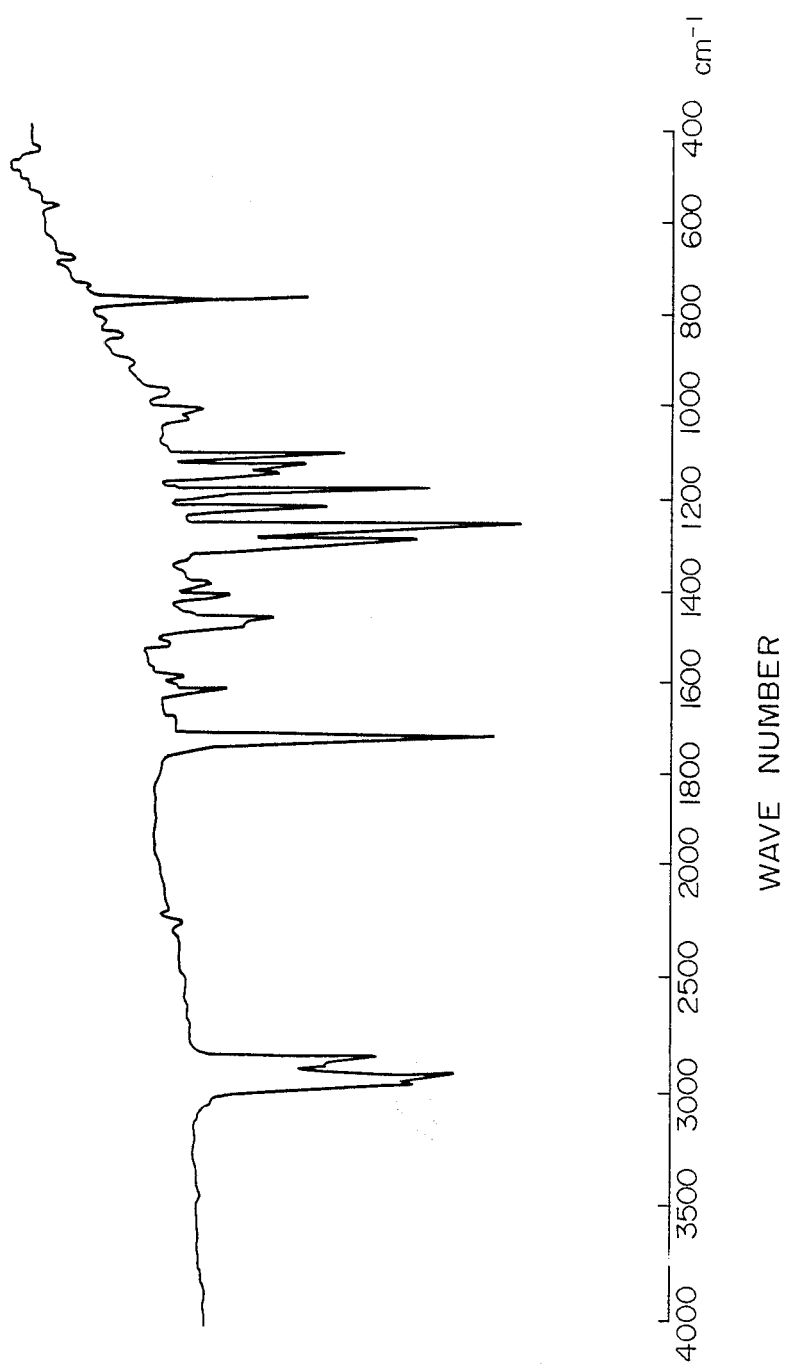
FIG. 6 is an IR spectrum of n-octyl 3,4-dimethylbenzoate.

(3) IR spectrum (neat) is shown in FIG. 6. The spectrum shows a absorption due to ester C=O stretching vibration near 1710 $cm^{-1}$.

EXAMPLE 1

[Synthesis of 6-methoxycarbonyl-2,3-dicyanonaphthalene]

To a solution of 33.8 g (0.2 mol) of methyl 3,4-dimethylbenzoate and 142.4 g (0.8 mol) of N-bromosuccinimide in 500 ml of carbon tetrachloride was added 1 g of benzoyl peroxide, and the resulting mixture was irradiated from a 100-W high pressure mercury arc lamp for 8 to 12 hours under reflux. After the mixture was allowed to cool, the white crystals precipitated were removed by filtration and the carbon tetrachloride solution, i.e., the mother liquor was concentrated under reduced pressure. The solid thus obtained was recrystallized from hexane/methylene chloride to obtain 79 g of methyl 3,4-bis(dibromomethyl)benzoate in the form of colorless crystals. Physical properties of methyl 3,4-bis(dibromomethyl)benzoate were as follows:

(1) Melting point: 99.5°–100.5° C.

| | (2) Elementary analysis values: | | |
|---|---|---|---|
| | C | H | Br |
| Calculated (%) | 25.03 | 1.68 | 66.62 |
| Found (%) | 25.07 | 1.54 | 65.72 |

Figure 7:
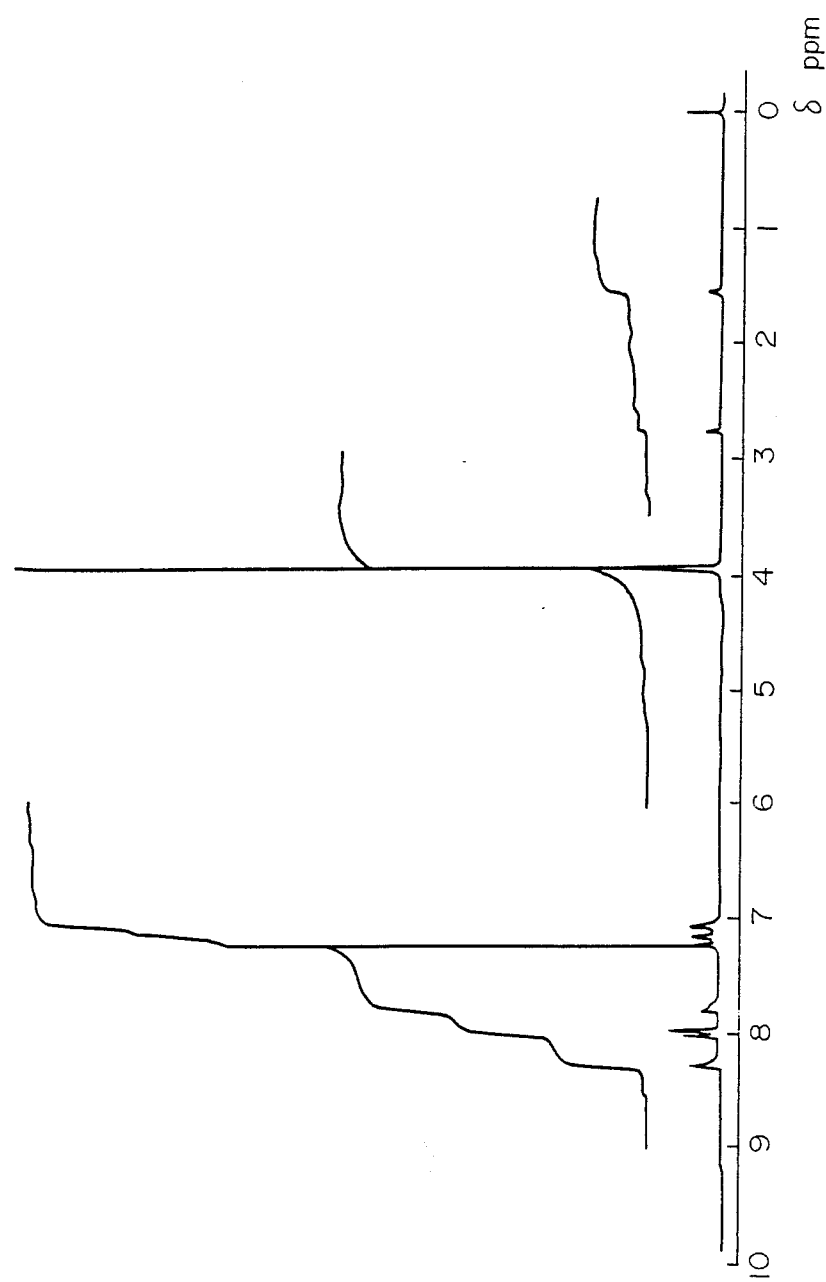
FIG. 7 is an NMR spectrum of methyl 3,4-bis(dibromomethyl)benzoate.

(3) NMR spectrum values (the NMR spectrum is shown in FIG. 7): $CDCl_3$ solvent: δ values 8.29 (1H, br-s), 8.03 (1H, dd, J=8.24, 1.53 Hz), 7.81 (1H, d, J=8.24 Hz), 7.18 (1H, br-s), 7.09 (1H, br-s), 3.96 (3H, s).

Figure 8:
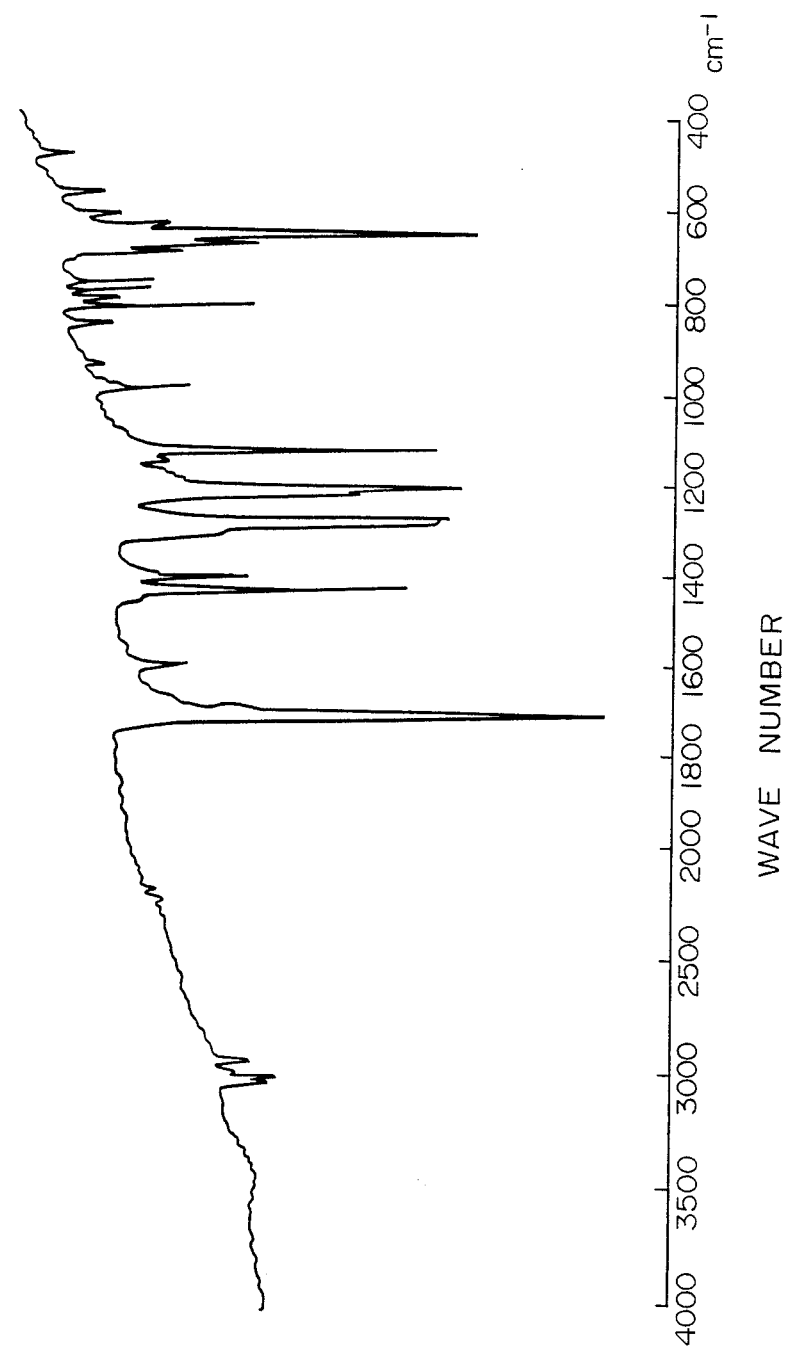
FIG. 8 is an IR spectrum of methyl 3,4-bis(dibromomethyl)benzoate.

(4) IR spectrum (KBr) is shown in FIG. 8.

The spectrum shows an absorption due to ester C=O stretching vibration near 1705 cm$^{-1}$.

Next, 100 g (0.67 mol) of sodium iodide was added to a solution of 48 g (0.1 mol) of the methyl 3,4-bis(dibromomethyl)benzoate obtained and 13.5 g (0.173 mol) of fumaronitrile in 400 ml of anhydrous N,N-dimethylformamide with sufficient stirring, and the resulting mixture was stirred in a nitrogen atmosphere at about 75° C. for about 7 hours. After completion of the reaction, the reaction mixture was poured onto about 2 Kg of ice. Sodium hydrogensulfite was slowly added until the reddish-brown aqueous solution thus obtained turned light-yellow. Sodium hydrogensulfite was added in a slight excess and after stirring for a while, the resulting mixture was allowed to stand overnight at room temperature. The light-yellow solid precipitated was filtered and was sufficiently washed with water and then methanol. The light-yellow solid was recrystallized from acetone/methanol to obtain 13.9 g of colorless needles. The crystal were identified as 6-methoxycarbonyl-2,3-dicyanonaphthalene from the following analysis results:

(1) Melting point: 264°–265° C.

| (2) Elementary analysis values: | | | |
|---|---|---|---|
| | C | H | N |
| Calculated (%) | 71.18 | 3.41 | 11.86 |
| Found (%) | 71.21 | 3.37 | 11.87 |

Figure 9:
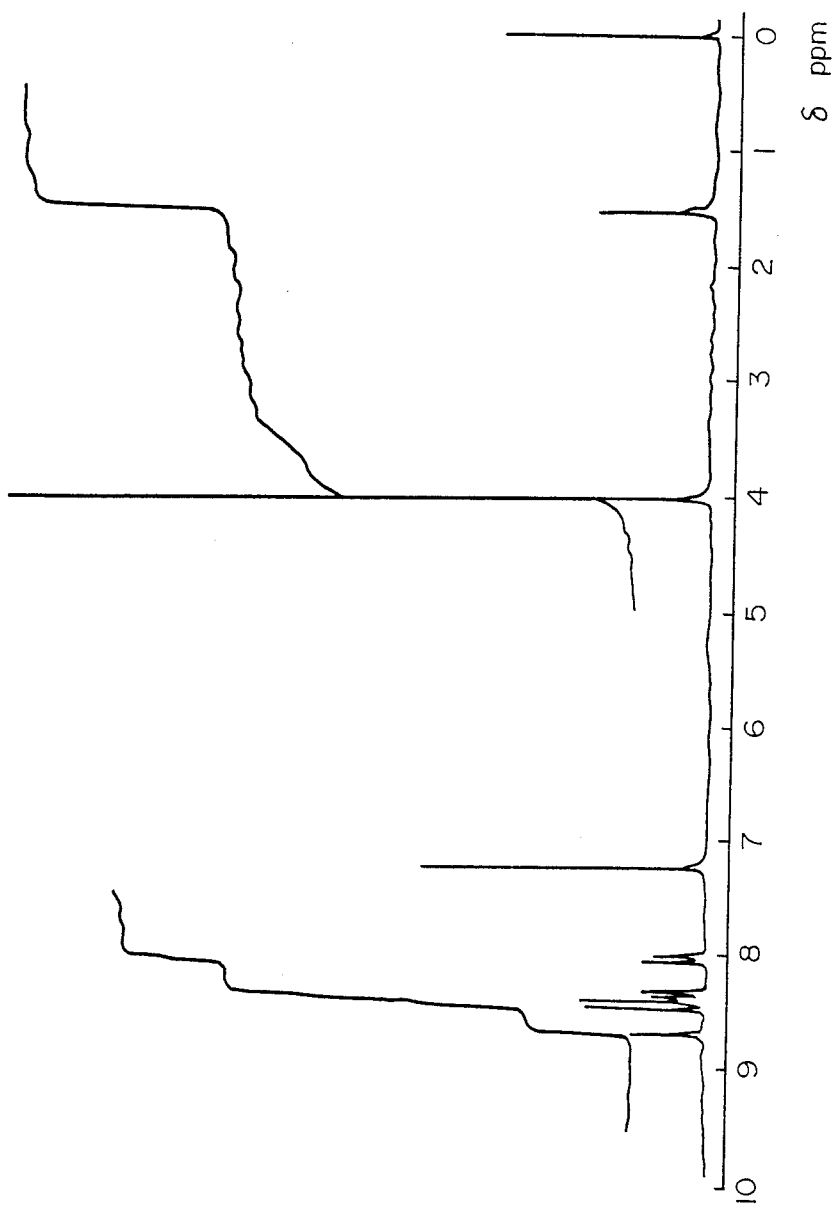
FIG. 9 is an NMR spectrum of 6-methoxycarbonyl-2,3-dicyanonaphthalene.

(3) NMR spectrum values (the NMR spectrum is shown in FIG. 9): CDCl$_3$ solvent: δ values 8.72 (1H, br-s), 8.47 (1H, s), 8.41 (1H, s), 8.38 (1H, dd, J=8.55, 1.53 Hz), 8.06 (1H, d, J=8.55 Hz), 4.04 (3H, s).

Figure 10:
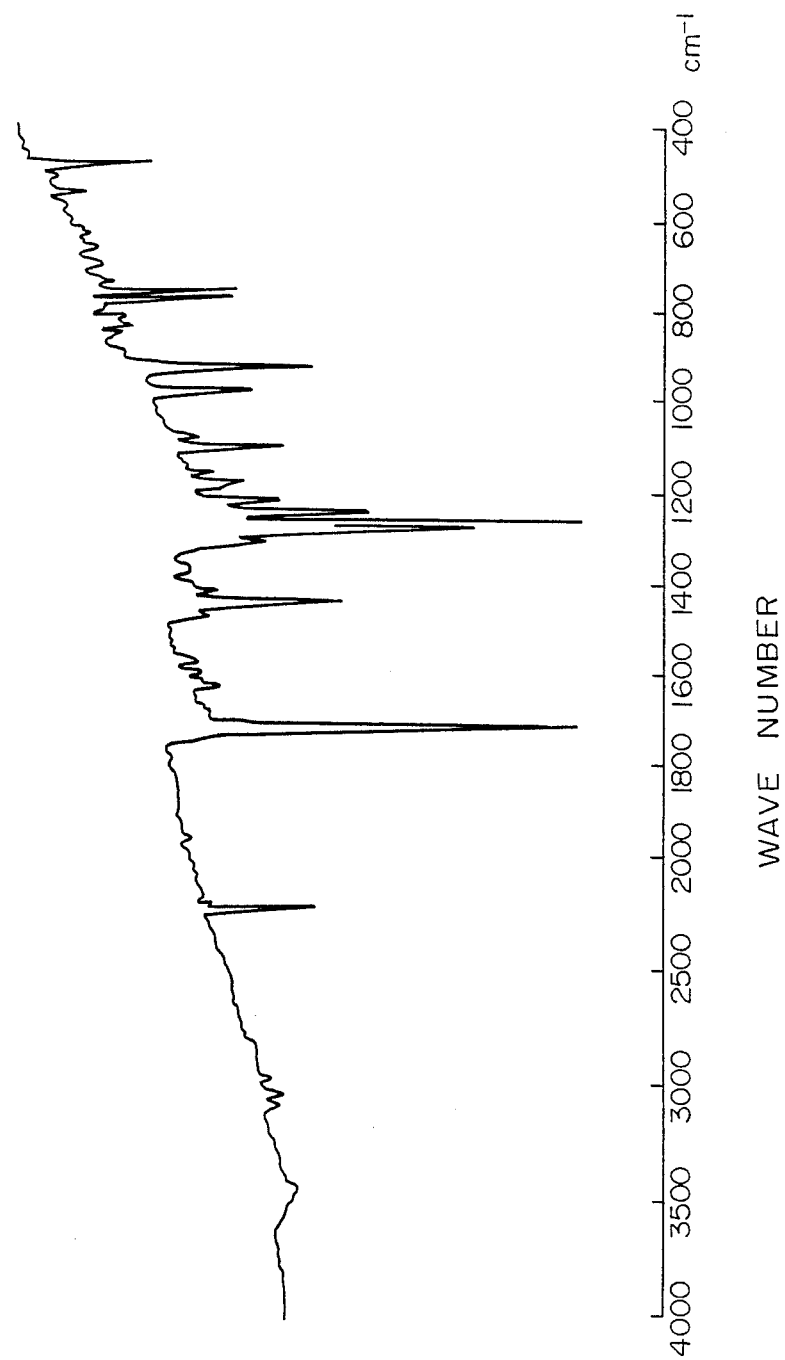
FIG. 10 is an IR spectrum of 6-methoxycarbonyl-2,3-dicyanonaphthalene.

(4) IR spectrum (KBr) is shown in FIG. 10.

The spectrum shows an absorption due to ester C=O stretching vibration near 1700 cm$^{-1}$.

EXAMPLE 2

[Synthesis of 6-(n-amyloxycarbonyl)-2,3-dicyanonaphthalene]

To a solution of 44.1 g (0.2 mol) of n-amyl 3,4-dimethylbenzoate and 142.4 g (0.8 mol) of N-bromosuccinimide in 500 ml of carbon tetrachloride was added 1 g of benzoyl peroxide, and the resulting mixture was irradiated from a 100-W high pressure mercury arc lamp for about 11 hours under reflux. After the mixture was allowed to cool, the white crystals precipitated were removed by filtration and the carbon tetrachloride solution, i.e., the mother liquor was sufficiently concentrated under reduced pressure. The light-brown oily substance thus obtained was dissolved in 800 ml of anhydrous N,N-dimethylformamide, and 27 g (0.346 mol) of fumaronitrile was added, followed by adding thereto 200 g (1.34 mol) of sodium iodide with sufficient stirring. The resulting mixture was stirred in a nitrogen atmosphere at 75° C. for about 7 hours. After completion of the reaction, the reaction mixture was poured onto about 4 Kg of ice. Sodium hydrogensulfite was slowly added until the reddish-brown aqueous solution thus obtained turned light-yellow. Sodium hydrogensulfite was added in a slight excess and after stirring for a while, the resulting mixture was allowed to stand overnight at room temperature. The light-yellow solid precipitated was filtered, and was washed sufficiently with water and then several times with methanol. The light-yellow solid thus treated was dissolved in about 500 ml of chloroform, and the chloroform layer was separated from the aqueous layer and then dried over anhydrous magnesium sulfate. The chloroform solution was concentrated under reduced pressure and then recrystallized twice from chloroform/ethanol to obtain 20 g of colorless needles. The crystals were identified as 6-(n-amyloxycarbonyl)-2,3-dicyanonaphthalene from the following analysis results:

(1) Melting point: 150°–152° C.

| (2) Elementary analysis values: | | | |
|---|---|---|---|
| | C | H | N |
| Calculated (%) | 73.95 | 5.52 | 9.58 |
| Found (%) | 73.82 | 5.38 | 9.51 |

(3) NMR spectrum values: CDCl$_3$ solvent: δ values 8.70 (1H, br-s), 8.49 (1H, s), 8.41 (H, s), 8.38 (1H, dd, J=8.55, 1.53 Hz), 8.06 (1H, d, J=8.55 Hz), 4.43 (2H, t, J=6.72 Hz), 1.84 (2H, quintet, J=6.72 Hz), 1.44 (4H, m), 0.96 (3H, t, J=6.7 Hz).

Figure 11:
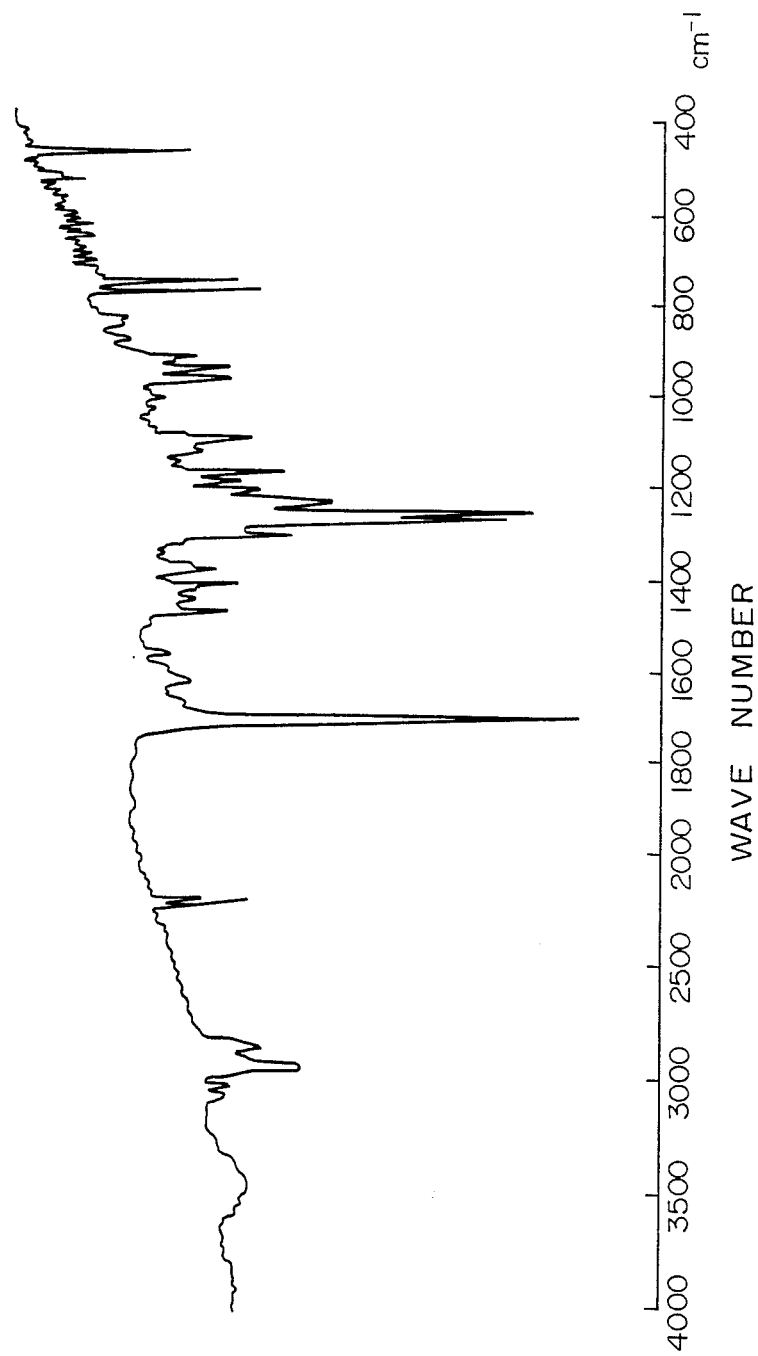
FIG. 11 is an IR spectrum of 6-(n-amyloxycarbonyl)-2,3-dicyanonaphthalene.

(4) IR spectrum (KBr method) is shown in FIG. 11.

The spectrum shows an absorption due to ester C=O stretching vibration near 1700 cm$^{-1}$.

EXAMPLE 3

[Synthesis of 6-(n-octyloxycarbonyl)-2,3-dicyanonaphthalene]

To a solution of 52.5 g (0.2 mol) of n-octyl 3,4-dimethylbenzoate and 142.2 g (0.8 mol) of N-bromosuccinimide in 500 ml of carbon tetrachloride was added 1 g of benzoyl peroxide, and the resulting mixture was irradiated from a 100-W high pressure mercury arc lamp for about 11 hours under reflux. After cooling, the reaction mixture was treated with fumaronitrile in the same manner as in Example 2. The reaction mixture thus obtained was treated in the same manner as in Example 2, and recrystallization from chloroform/ethanol was repeated several times to obtain about 7 g of colorless needles. The crystals were identified as 6-(n-octyloxycarbonyl)-2,3-dicyanonaphthalene from the following analysis results:

(1) Melting point: 142°–144° C.

| (2) Elementary analysis values: | | | |
|---|---|---|---|
| | C | H | N |
| Calculated (%) | 75.42 | 6.63 | 8.38 |
| Found (%) | 75.20 | 6.41 | 7.99 |

(3) NMR spectrum values: CDCl$_3$ solvent: δ values 8.70 (1H, br-s), 8.49 (1H, s), 8.42 (1H, s), 8.38 (1H, dd, J=8.55, 1.52 Hz), 8.06 (1H, d, J=8.55 Hz), 4.42 (2H, t, J=6.72 Hz), 1.83 (2H, quintet, J=6.72 Hz), 1.2–1.6 (10H, m), 0.89 (3H, t, J=6.72 Hz).

Figure 12:
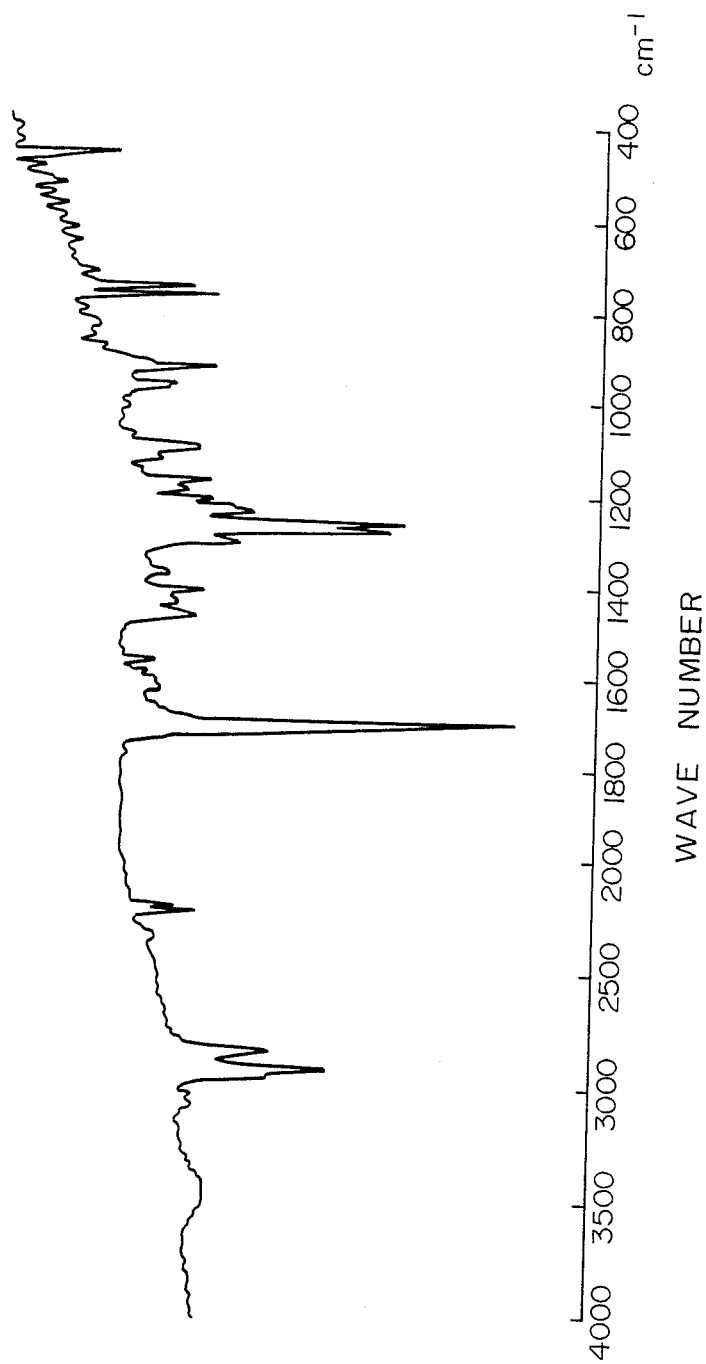
FIG. 12 is an IR spectrum of 6-(n-octyloxycarbonyl)-2,3-dicyanonaphthalene.

(4) IR spectrum (KBr) is shown in FIG. 12.

The spectrum shows an absorption due to ester C=O stretching vibration near 1,700 cm$^{-1}$.

COMPARATIVE EXAMPLE 1

[Synthesis of tetra(n-butoxy) vanadyl naphthalocyanine]

25 Grams (0.1 mol) of 6-n-butoxy-2,3-dicyanonaphthalene, 6 g (0.035 mol) of vanadium trichloride and 75 g of urea were reacted with one another at 195° to 200° C. for 2 hours. After cooling, the reaction mixture solidified was added to 500 ml of hydrochloric acid and after stirring at 80° C. for minutes, solids were collected therefrom by filtration, treated with 500 ml of 5% hydrochloric acid again, and washed with hot water.

Subsequently, a cake collected by filtration of the washed solids was added to 300 ml of a 10% aqueous sodium hydroxide solution and after stirring at 80° C. for 30 minutes, solids were collected therefrom by filtration, treated with 300 ml of a 10% aqueous sodium hydroxide solution again, and washed with hot water.

Then, the cake thus treated was added to 300 ml of methanol and after reflux, solids were collected therefrom by filtration and dried to obtain 15 g of a crude product. The crude product was dissolved in 500 ml of toluene and the insoluble materials were removed by filtration, after which the residue was purified by a column chromatography to obtain 6 g of a purified product in the form of yellowish-green powder.

COMPARATIVE EXAMPLE 2

[production of tetra-tert-amyl vanadyl naphthalocyanine]

15 Grams of 6-tert-amyl-2,3-dicyanonaphthalene, 3.8 g of vanadium trichloride and 70 g of urea were reacted with one another at 195° to 200° C. for 2 hours. After cooling, 300 ml of 5% hydrochloric acid was added to the reaction mixture solidified. On heating at 50° C., the solidified mixture was gradually loosened. After stirring at 50° C. for 30 minutes, the insoluble materials were collected by filtration and the filter cake thus obtained was treated with 300 ml of 5% hydrochloric acid again and then washed with hot water. Subsequently, the filter cake was stirred together with 200 ml of a 10% aqueous sodium hydroxide solution at 70° C. for 30 minutes, after which the insoluble materials were collected by filtration. The filter cake thus obtained was treated with 200 ml of a 10% aqueous sodium hydroxide solution again and then sufficiently washed with hot water. Then, the filter cake was refluxed together with 200 ml of methanol with heating for 30 minutes, after which the insoluble materials were collected by filtration and dried to obtain 10 g of a crude product. Subsequently, the crude product was stirred together with 300 ml of toluene at 80° C. for 30 minutes, and then the insoluble materials were removed by filtration and the toluene solution was subjected to column chromatography on silica gel to obtain 2.4 g of a purified product.

EXAMPLE 4

[Synthesis of 6-(n-octadecyloxycarbonyl)-2,3-dicyanonaphthalene]

3.14 Grams (13.3 m mols) of 6-methoxycarbonyl-2,3-dicyanonaphthalene and 3.6 g (13.3 m mols) of 1-octadecanol were refluxed in 40 ml of benzene in the presence of 2.2 g (11.6 m mols) of p-toluenesulfonic acid monohydrate for about 6 hours, with continuous extraction of water and methanol by use of Molecular Sieves 3A. After the reaction mixture was allowed to cool, about 150 ml of chloroform was added and the resulting chloroform solution wa washed three times with a saturated aqueous sodium hydrogencarbonate solution and then three times with water, and dried over anhydrous sodium sulfate. The chloroform solution was concentrated and then purified by a silica gel column chromatography by using benzene as an eluent. The colorless solid thus obtained was recrystallized from ethanol/chloroform to obtain 0.68 g of colorless needles. The colorless crystals were identified as 6-(n-octadecyloxycarbonyl)-2,3-dicyanonaphthalene from the following analysis results:

(1) Melting point: 139°–140° C.

| (2) Elementary analysis values: | | | |
|---|---|---|---|
| | C | H | N |
| Calculated (%) | 78.44 | 8.92 | 5.90 |
| Found (%) | 78.52 | 9.05 | 5.87 |

Figure 13:
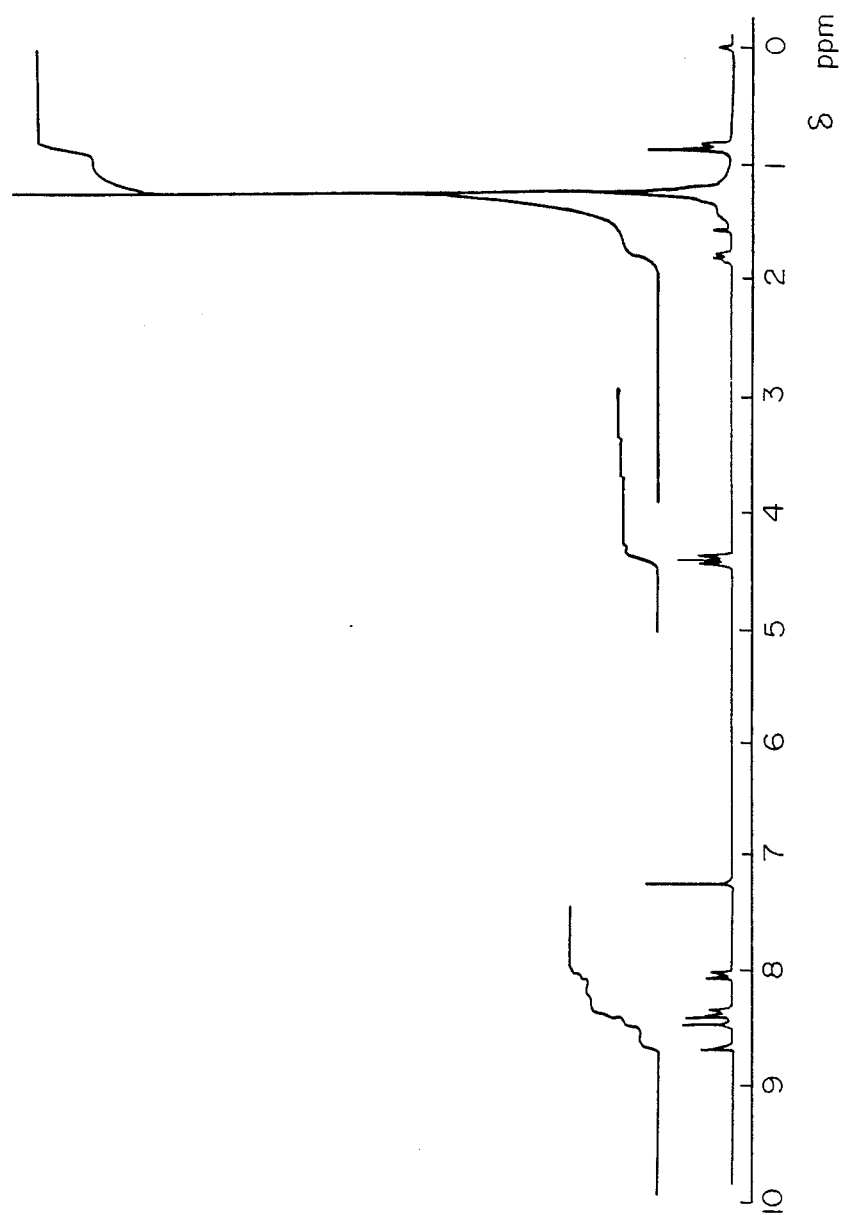
FIG. 13 is an NMR spectrum of 6-(n-octadecyloxycarbonyl)-2,3-dicyanonaphthalene.

(3) NMR values (the NMR spectrum is shown in FIG. 13): CDCl$_3$ solvent: δ values 8.71 (1H, br-s), 8.49 (1H, s), 8.42 (1H, s), 8.38 (1H, dd, J=8.55, 1.53 Hz), 8.06 (1H, d, J=8.55 Hz), 4.42 (2H, t, J=6.72 Hz), 1.83 (2H, quintet, J=6.72 Hz), 1.25 (30H, br-s), 0.88 (3H, t, J=6.72 Hz).

Figure 14:
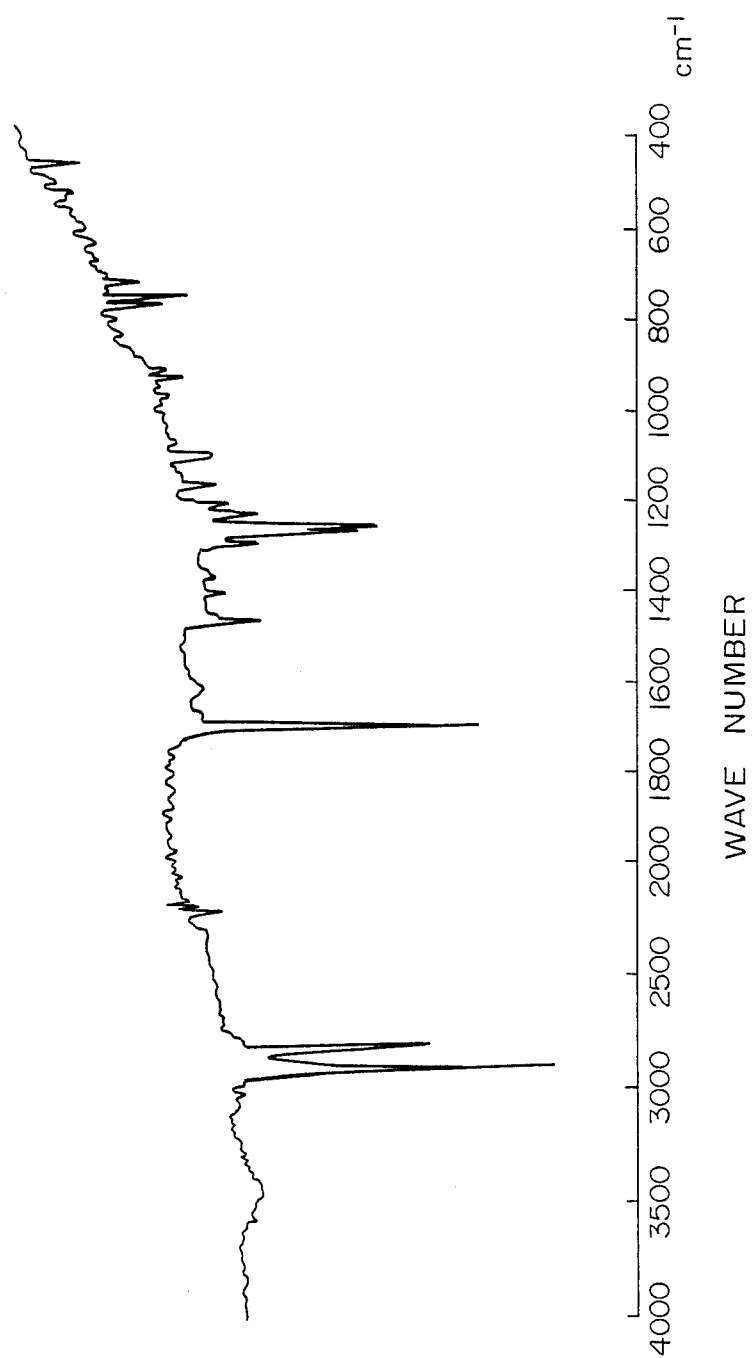
FIG. 14 is an IR spectrum of 6-(n-octadecyloxycarbonyl)-2,3-dicyanonaphthalene.

(4) IR spectrum (KBr) is shown in FIG. 14.

The spectrum shows an absorption due to ester C=O stretching vibration near 1700 cm$^{-1}$.

EXAMPLE 5

[Synthesis of 6-(n-tetradecyloxycarbonyl)-2,3-dicyanonaphthalene]

236 Milligrams (1 mmol) of 6-methoxycarbonyl-2,3-dicyanonaphthalene and 10.72 g (50 mmols) of 1-tetradecanol were refluxed in 100 ml of benzene in the presence of 1.94 g (10 mmols) of p-toluenesulfonic acid monohydrate for about 12 hours with continuous extraction of water and methanol by use of Molecular Sieves 3A. After the reaction mixture was allowed to cool, the benzene solvent was removed by distillation and the residue was purified by a silica gel column chromatography by using toluene/chloroform (1:1 by volume) as an eluent.

Further, the purified product was recrystallized from acetone/methanol to obtain 103 mg of white crystals. The white crystals were identified as 6-(n-tetradecyloxycarbonyl)-2,3-dicyanonaphthalene from the following analysis results (1) Melting point: 142.0°–142.5° C.

| (2) Elementary analysis values: | | | |
|---|---|---|---|
| | C | H | N |
| Calculated (%) | 77.48 | 8.19 | 6.69 |
| Found (%) | 77.53 | 8.11 | 6.76 |

Figure 15:
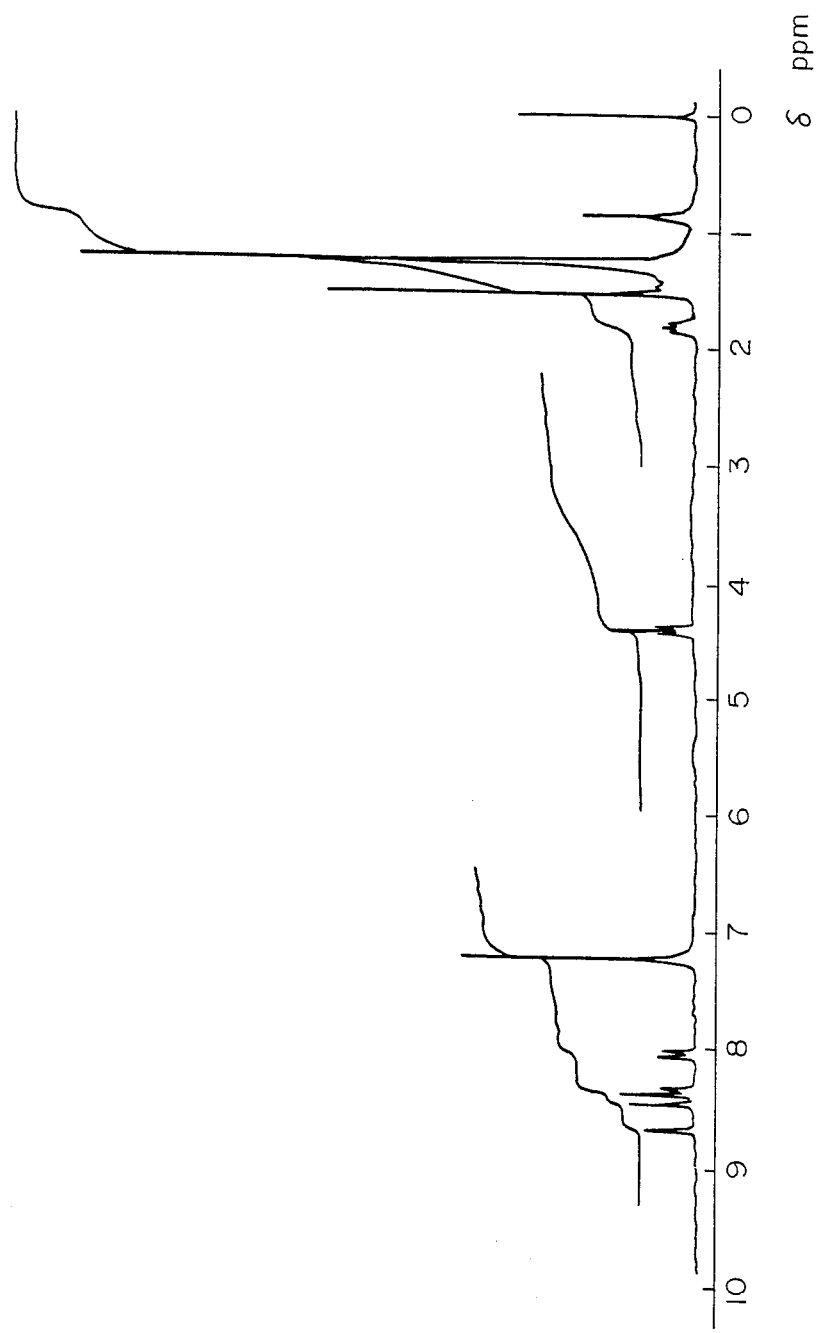
FIG. 15 is an NMR spectrum of 6-(n-tetradecyloxycarbonyl)-2,3-dicyanonaphthalene.

(3) NMR values (the NMR spectrum is shown in FIG. 15): CDCl$_3$ solvent: δ values 8.68 (1H, br-s), 8.47 (1H, s), 8.39 (1H, s), 8.36 (1H, dd, J=8.85, 1.52 Hz), 8.04 (1H, d, J=8.85 Hz), 4.40 (2H, t, J=6.71 Hz), 1.81 (2H, quintet, J=6.71 Hz), 1.25 (22H, br-s), 0.87 (3H, t, J=6.71 Hz).

Figure 16:
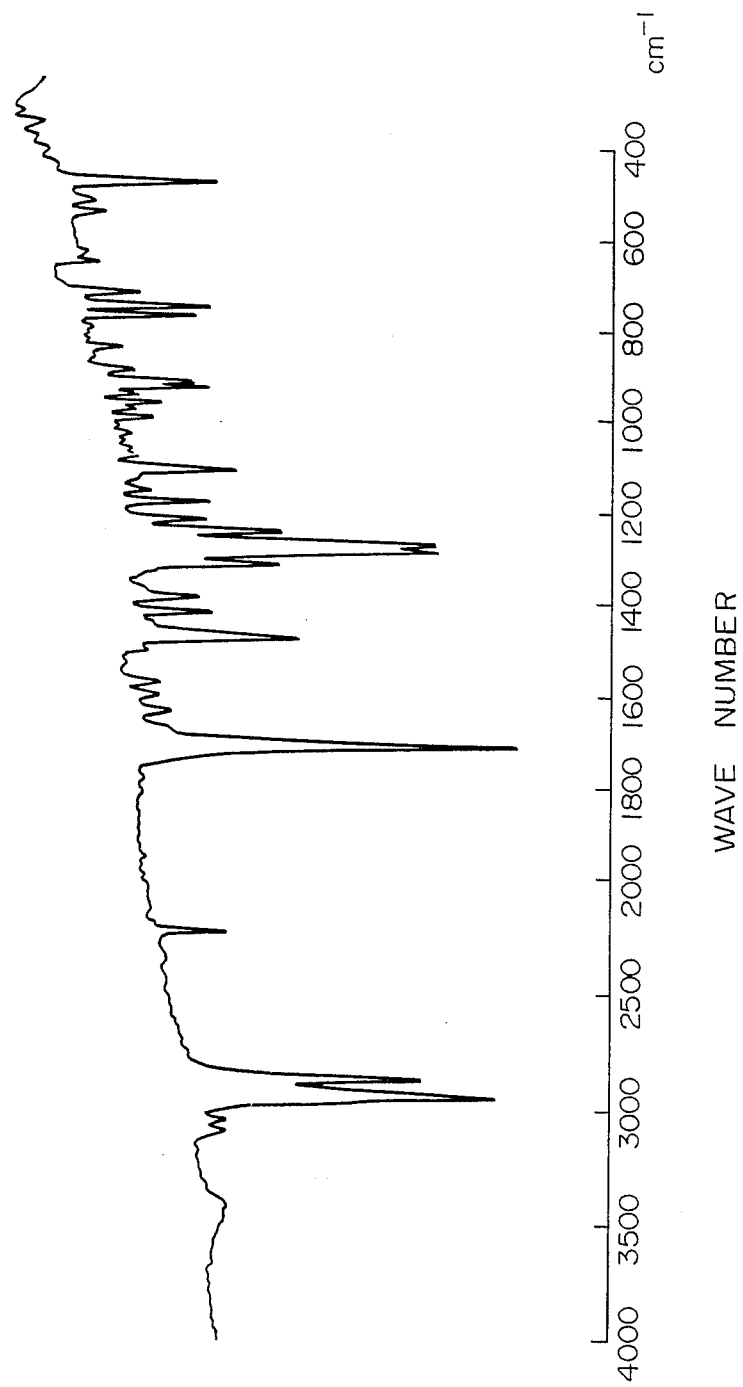
FIG. 16 is an IR spectrum of 6-(n-tetradecyloxycarbonyl)-2,3-dicyanonaphthalene.

(4) IR spectrum (KBr) is shown in FIG. 16.

The spectrum shows an absorption due to ester C=O stretching vibration near 1710 cm$^{-1}$.

[Synthesis of 6-(n-hexadecyloxycarbonyl)-2,3-dicyanonaphthalene]

236 Milligrams (1 mmol) of 6-methoxycarbonyl-2,3-dicyanonaphthalene and 12.12 g (50 mmols) of 1-hexadecanol were refluxed in 100 ml of benzene in the presence of 1.94 g (10 mmols) of p-toluenesulfonic acid monohydrate for about 12 hours, with continuous extraction of water and methanol by use of Molecular Sieves 3A. After the reaction mixture was allowed to cool, the benzene was removed by distillation and the residue was purified by a silica gel column chromatography by using toluene/chloroform (1:1 by volume) as an eluent. Further, the purified product was recrystallized from acetone/methanol to obtain 247 mg of white crystals. The white crystals were identified as 6-(n-hexadecyloxycarbonyl)-2,3-dicyanonaphthalene from the following analysis results:

(1) Melting point: 140.7°–142.0° C.

| (2) Elementary analysis values: | | | |
|---|---|---|---|
| | C | H | N |
| Calculated (%) | 77.99 | 8.58 | 6.27 |
| Found (%) | 78.07 | 8.51 | 6.19 |

Figure 17:
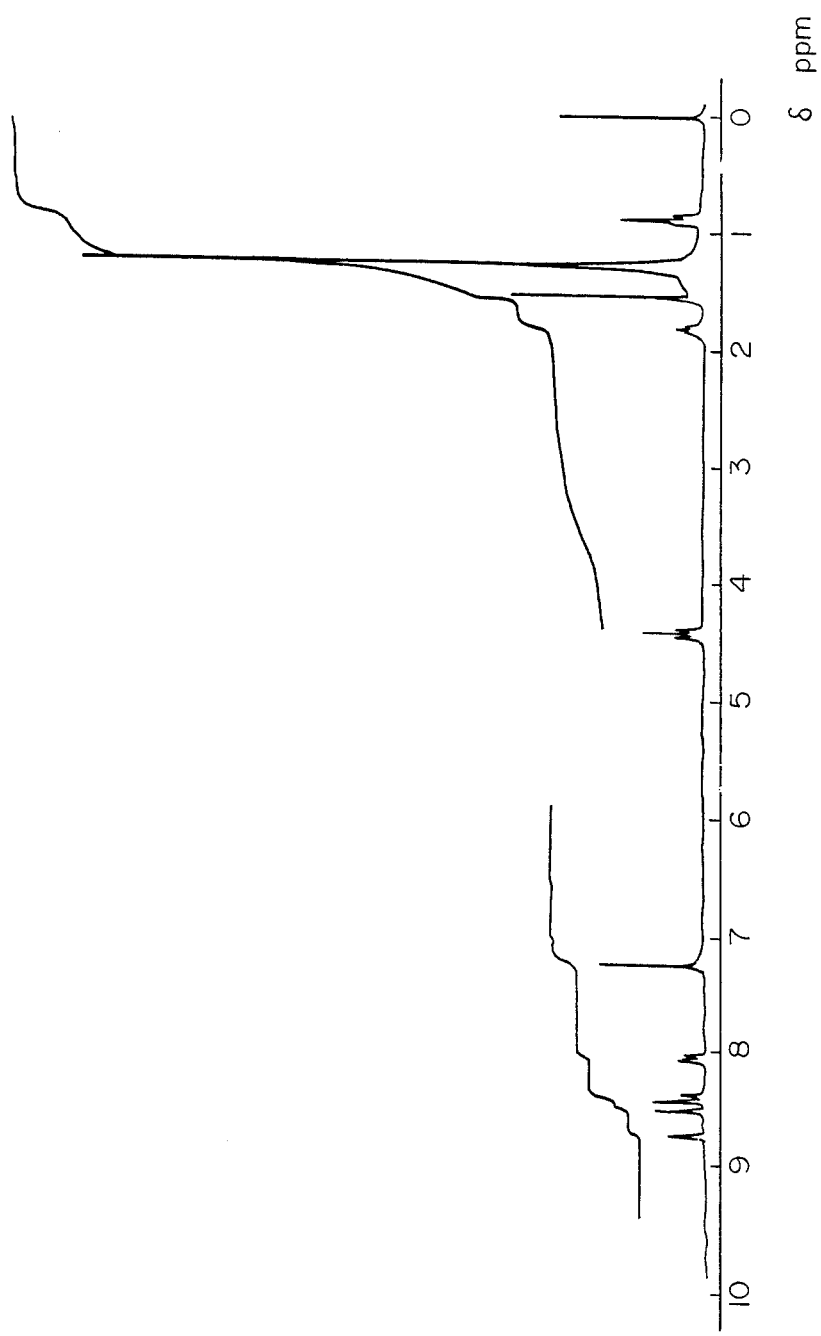
FIG. 17 is an NMR spectrum of 6-(n-hexadecyloxycarbonyl)-2,3-dicyanonaphthalene.

(3) NMR values (the NMR spectrum is shown in FIG. 17): $CDCl_3$ solvent: δ values 8.69 (1H, br-s), 8.47 (1H, s), 8.39 (1H, s), 8.37 (1H, dd, J=8.55, 1.53 Hz), 8.04 (1H, d, J=8.55 Hz), 4.41 (2H, t, J=6.72 Hz), 1.81 (2H, quintet, 6.72 Hz), 1.25 (26H, br-s), 0.87 (3H, t, J=6.72 Hz).

Figure 18:
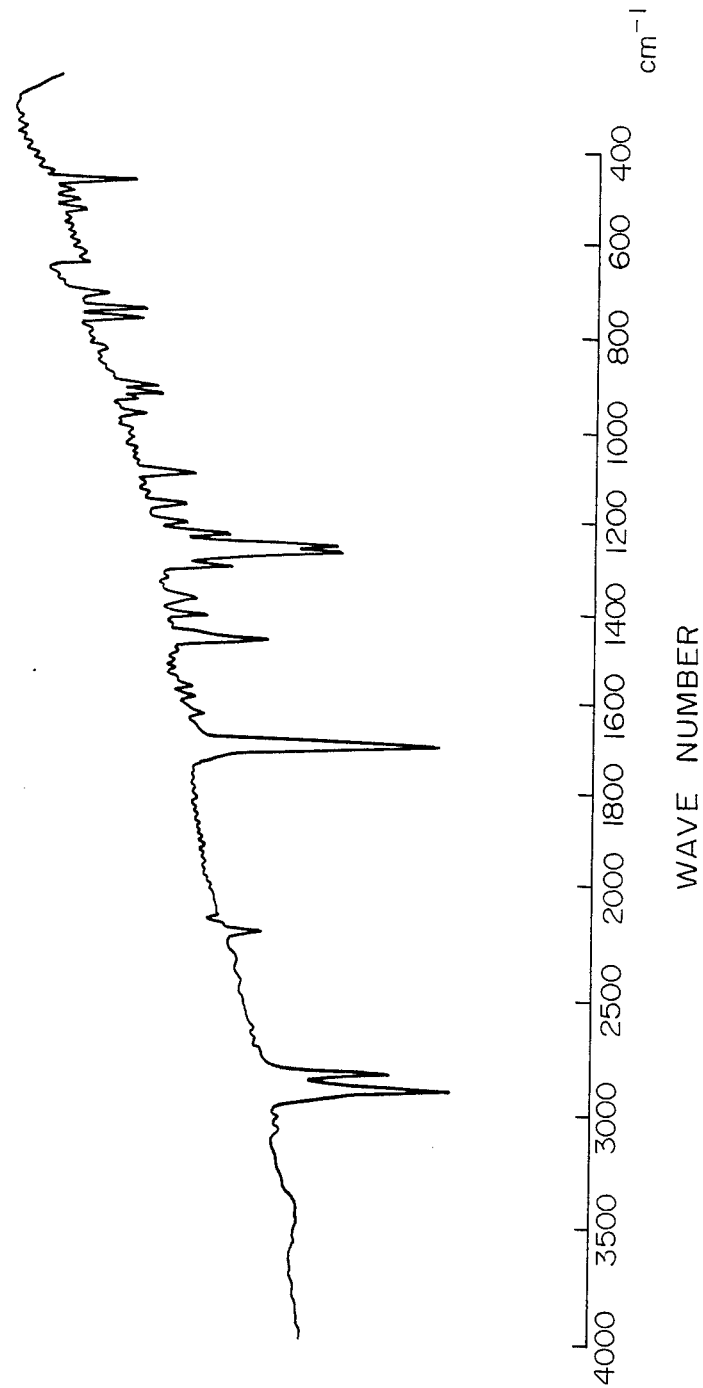
FIG. 18 is an IR spectrum of 6-(n-hexadecyloxycarbonyl)-2,3-dicyanonaphthalene.

(4) IR spectrum (KBr) is shown in FIG. 18.

The spectrum shows an absorption due to ester C=O stretching vibration near 1710 $cm^{-1}$.

EXAMPLE 7

[Synthesis of 6-(n-eicosyloxycarbonyl)-2,3-dicyanonaphthalene]

236 Milligrams (1 m mol) of 6-methoxycarbonyl-2,3-dicyanonaphthalene and 15.63 g (50 m mols) of 1-eicosanol were refluxed in 100 ml of benzene in the presence of 1.94 g (10 mmols) of p-toluenesulfonic acid monohydrate for about 28 hours, with continuous extraction of water and methanol by use of Molecular Sieves 3A. After the reaction mixture was allowed to cool, the benzene was removed by distillation and the residue was purified by a silica gel chromatography by using toluene/n-hexane (4/1 by volume) as an eluent. Further, the purified product was recrystallized from acetone/methanol to obtain 166 mg of white crystals. The white crystals were identified as 6-(n-eicosyloxycarbonyl)-2,3-dicyanonaphthalene from the following analysis results:

(1) Melting point: 138.0°–138.5° C.

| (2) Elementary analysis values: | | | |
|---|---|---|---|
| | C | H | N |
| Calculated (%) | 78.84 | 9.22 | 5.57 |
| Found (%) | 78.89 | 9.31 | 5.52 |

Figure 19:
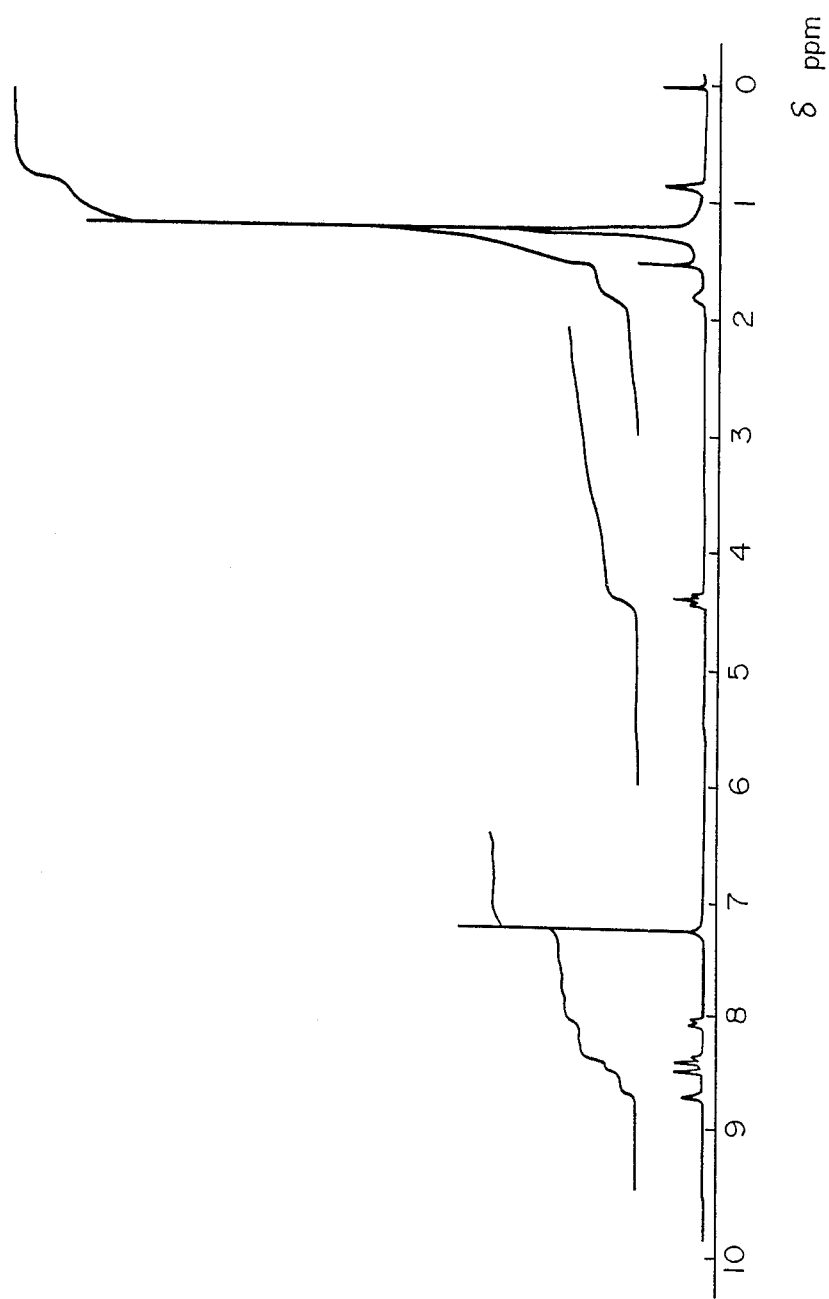
FIG. 19 is an NMR spectrum of 6-(n-eicosyloxycarbonyl)-2,3-dicyanonaphthalene.

(3) NMR values (the NMR spectrum is shown in FIG. 19): $CDCl_3$ solvent: δ values 8.70 (1H, br-s), 8.48 (1H, s), 8.41 (1H, s), 8.38 (1H, dd, J=8.85, 1.52 Hz), 8.05 (1H, d, J=8.85 Hz), 4.42 (2H, t, J=6.71 Hz), 1.83 (2H, quintet, J=6.71 Hz), 1.25 (34H, br-s), 0.88 (3H, t, J=6.71 Hz).

Figure 20:
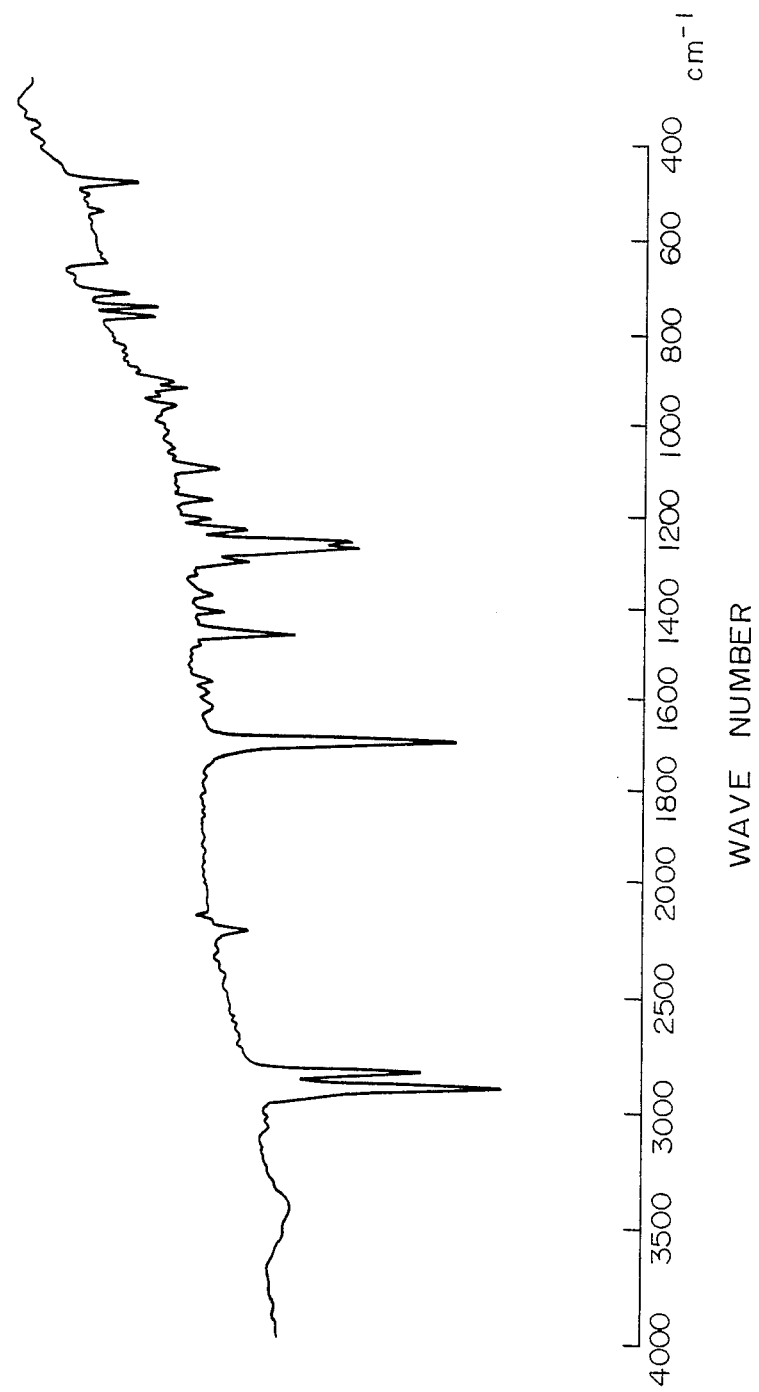
FIG. 20 is an IR spectrum of 6-(n-eicosyloxycarbonyl)-2,3-dicyanonaphthalene.

(4) IR spectrum (KBr) is shown in FIG. 20.

The spectrum shows an absorption due to ester C=O stretching vibration near 1710 $cm^{-1}$.

EXAMPLE 8

[Synthesis of 6-(n-docosyloxycarbonyl)-2,3-dicyanonaphthalene]

236 Milligrams (1 m mol) of 6-methoxycarbonyl-2,3-dicyanonaphthalene and 16.33 g (50 m mols) of 1-docosanol were refluxed in 100 ml of benzene in the presence of 1.94 g (10 m mols) of p-toluenesulfonic acid monohydrate for about 28 hours, with continuous extraction of water and methanol by use of Molecular Sieves 3A. After the reaction mixture was allowed to cool, the benzene solvent was removed by distillation and the residue was purified by a silica gel chromatography by using toluene/n-hexane (4/1 by volume) as an eluent. Further, the purified product was recrystallized from acetone/methanol to obtain 162 mg of white crystals. The white crystals were identified as 6-(n-docosyloxycarbonyl)-2,3-dicyanonaphthalene from the following analysis results:

(1) Melting point: 135° C.–136.5° C.

| (2) Elementary analysis values: | | | |
|---|---|---|---|
| | C | H | N |
| Calculated (%) | 79.20 | 9.49 | 5.28 |
| Found (%) | 79.12 | 9.57 | 5.14 |

Figure 21:
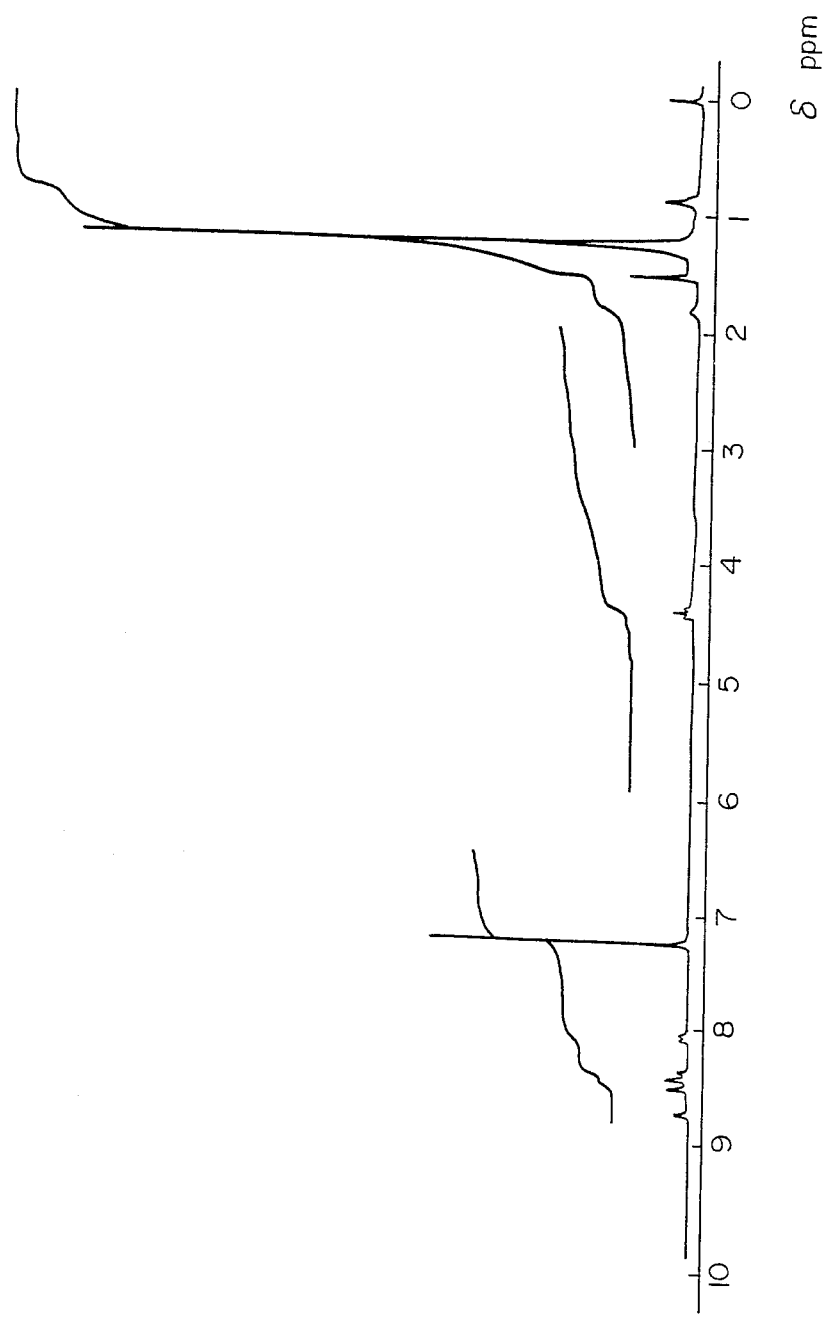
FIG. 21 is an NMR spectrum of 6-(n-docosyloxycarbonyl)-2,3-dicyanonaphthalene.

(3) NMR values (the NMR spectrum is shown in FIG. 21): $CDCl_3$ solvent: δ values 8.70 (1H, br-s), 8.48 (1H, s), 8.41 (1H, s), 8.37 (1H, dd, J=8.55, 1.53 Hz), 8.05 (1H, d, J=8.55 Hz), 4.42 (2H, t, J=6.72 Hz), 1.83 (2H, quintet, J=6.72 Hz), 1.25 (38H, br-s), 0.88 (3H, t, J=6.72 Hz).

Figure 22:
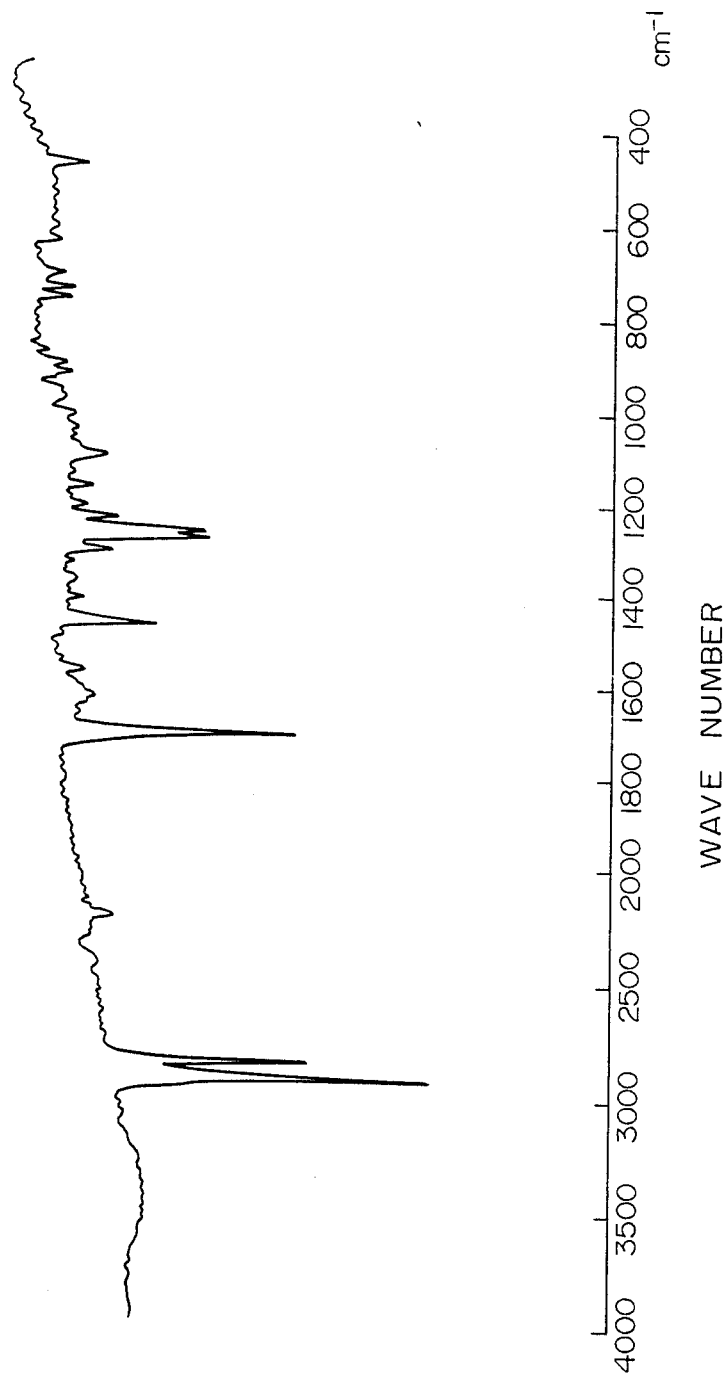
FIG. 22 is an IR spectrum of 6-(n-docosyloxycarbonyl)-2,3-dicyanonaphthalene.

(4) IR spectrum (KBr) is shown in FIG. 22.

The spectrum shows an absorption due to ester C=O stretching vibration near 1710 $cm^{-1}$.

APPLICATION EXAMPLE 1

[Synthesis of tetrakis(n-amyloxycarbonyl) vanadyl naphthalocyanine]

1.46 Grams (5 mmols) of 6-(n-amyloxycarbonyl)-2,3-dicyanonaphthalene, 0.32 g (2.01 mmols) of vanadium trichloride, 10 mg of ammonium molybdate and 5 g of urea were reacted with one another with sufficient stirring at about 220° C. for about 2.5 hours. After the reaction mixture was allowed to cool, 40 ml of 5% hydrochloric acid was added to the reaction mixture solidified to loosen the mixture to a certain extent, followed by sufficient stirring at about 50° C. for 30 minutes. After the stirring, the insoluble materials were filtered and the residue was sufficiently washed successively with water, methanol and acetone. From the solid thus obtained, impurities were extracted by means of a Soxhlet extractor for about 50 hours by using a mixed solvent of methanol and acetone (1:1). Next, Soxhlet extraction was carried out for 20 hours by using chloroform in place of the mixed solvent. The dark-green chloroform solution thus obtained was filtered by suction with heating, after which the residue was concentrated to dryness under reduced pressure to obtain 861 mg of black crystals. The crystals were identified as tetrakis(namyloxycarbonyl) vanadyl naphthalocyanine from the following analysis results:

(1) Melting point >300° C.

| (2) Elementary analysis values: | | | |
|---|---|---|---|
| | C | H | N |
| Calculated (%) | 69.95 | 5.22 | 9.06 |
| Found (%) | 70.13 | 5.14 | 9.33 |

Figure 23:
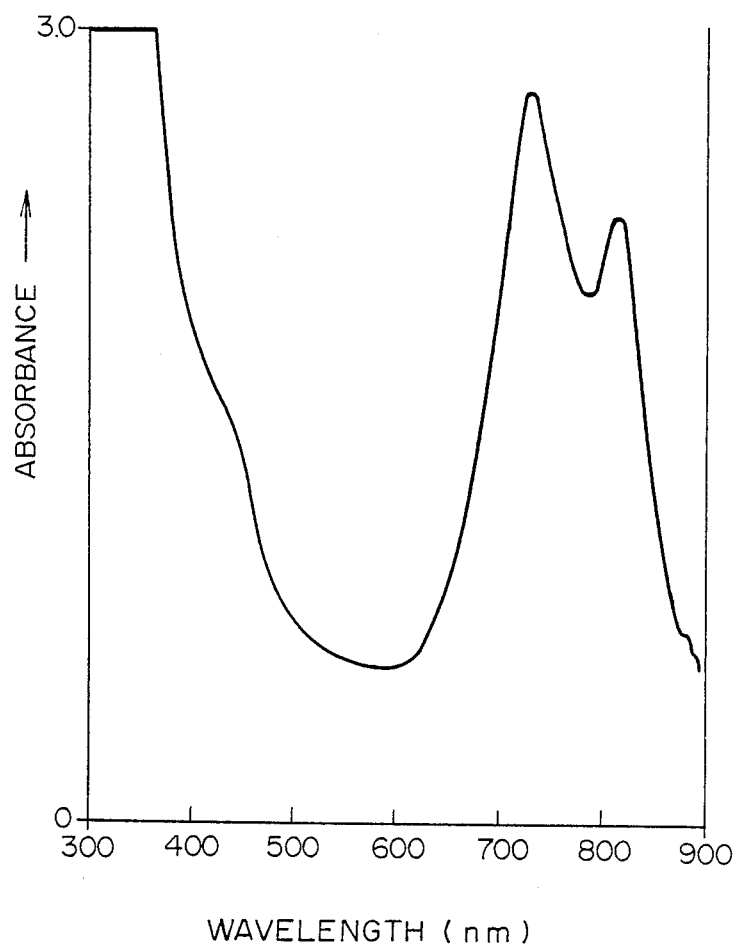
FIG. 23 is an electronic spectrum of tetrakis(n-amyloxycarbonyl) vanadyl naphthalocyanine.

(3) Electronic spectrum ($CHCl_3$ solution) is shown in FIG. 23.

Figure 24:
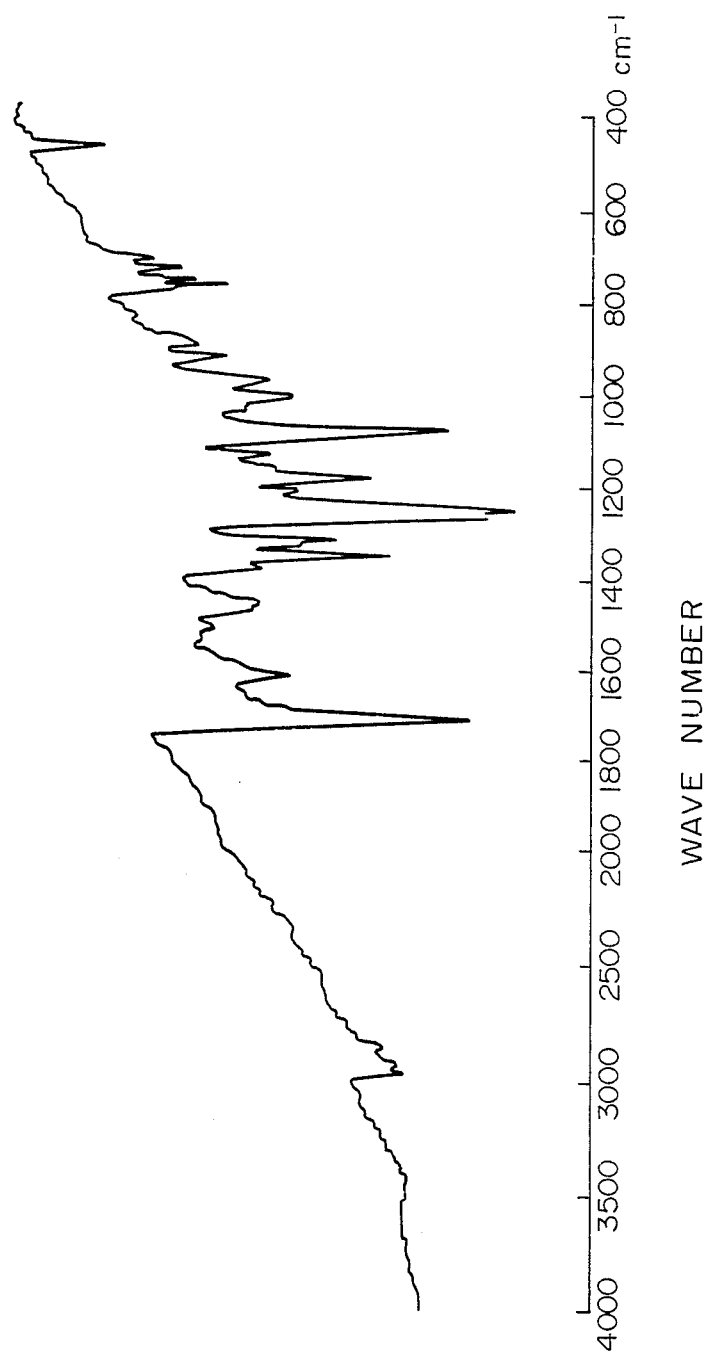
FIG. 24 is an IR spectrum of tetrakis(n-amyloxycarbonyl) vanadyl naphthalocyanine.

(4) IR spectrum (KBr) is shown in FIG. 24.

The spectrum shows an absorption due to ester C=O stretching vibration near 1700 cm$^{-1}$.

APPLICATION EXAMPLE 2

[Synthesis of tetrakis(n-amyloxycarbonyl) copper naphthalocyanine]

1.46 Grams (5 mmols) of 6-(n-amyloxycarbonyl)-2,3-dicyanonaphthalene, 273 mg (1.6 mmol) of cupric chloride dihydrate, 10 mg of ammonium molybdate and 5 g of urea were reacted with one another with sufficient stirring at about 220° C. for about 2.5 hours. After being allowed to cool, the reaction mixture was treated in the same manner a in Application Example 1 to obtain 987 mg of black crystals. The crystals were identified as tetrakis(n-amyloxycarbonyl) copper naphthalocyanine from the following analysis results:

(1) Melting point >300° C.

| (2) Elementary analysis: | | | |
|---|---|---|---|
| | C | H | N |
| Calculated (%) | 70.14 | 5.23 | 9.09 |
| Found (%) | 69.45 | 5.20 | 9.17 |

Figure 25:
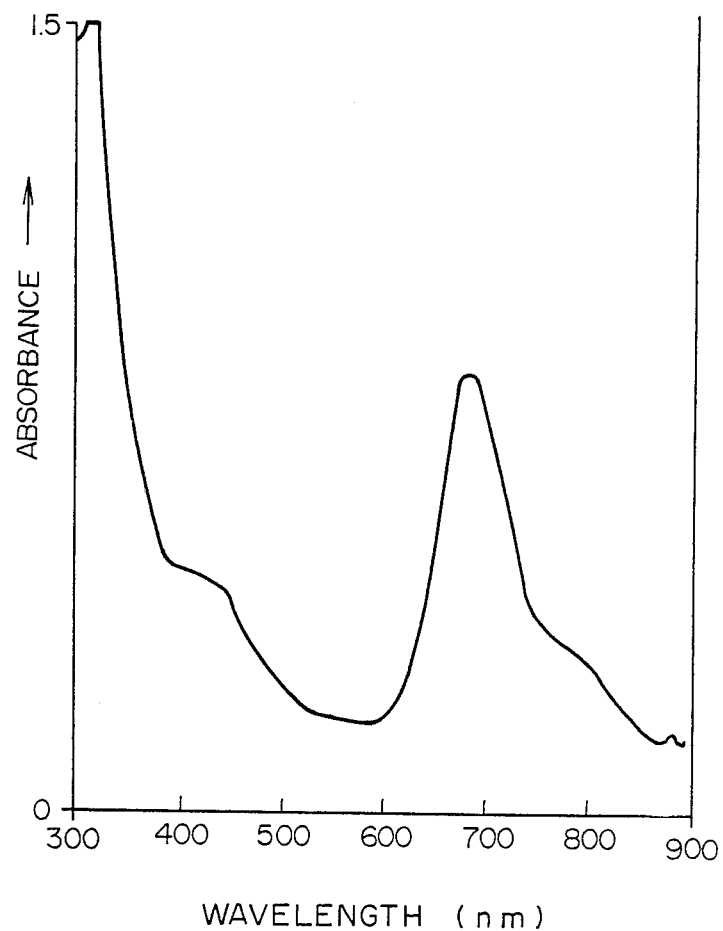
FIG. 25 is an electronic spectrum of tetrakis(n-amyloxycarbonyl) copper naphthalocyanine.
Figure 26:
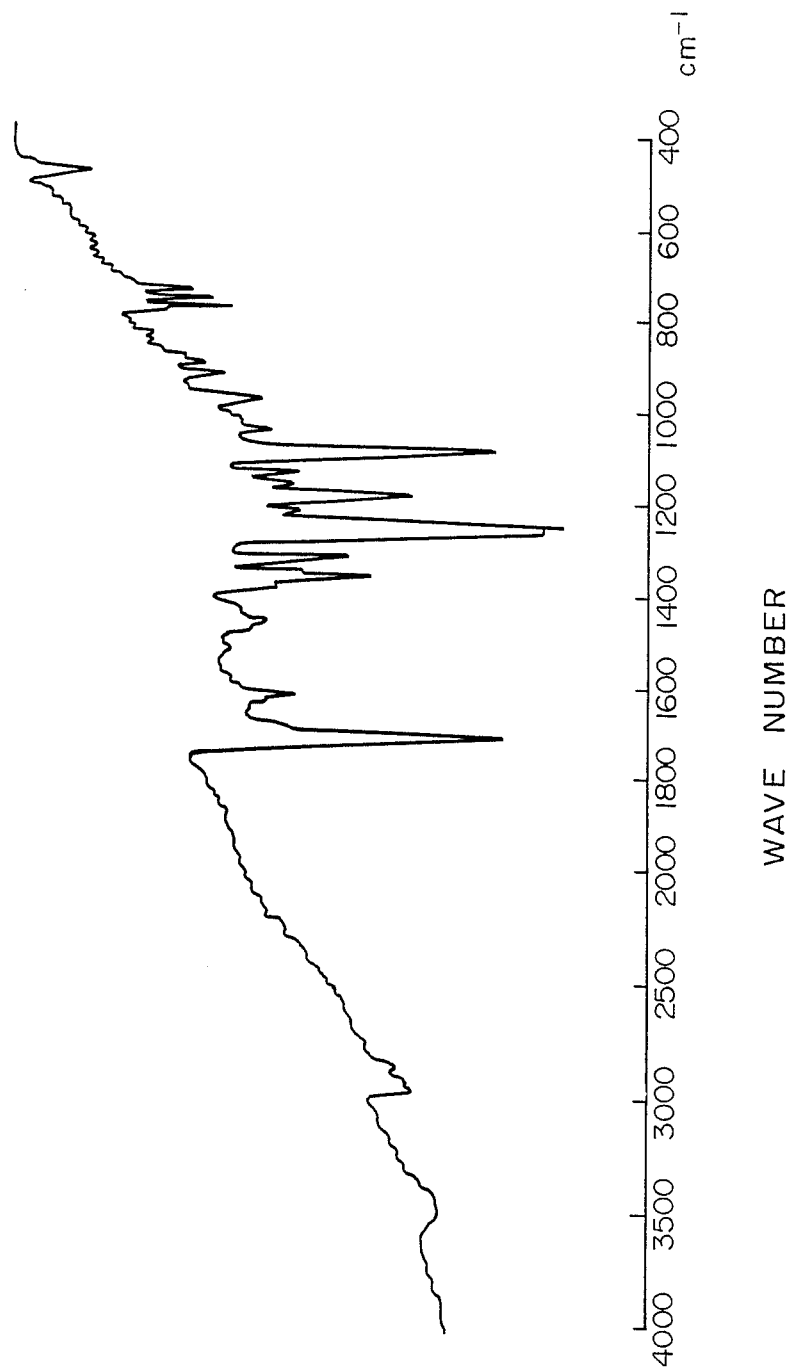
FIG. 26 is an IR spectrum of tetrakis(n-amyloxycarbonyl) copper naphthalocyanine.

(3) Electronic spectrum (CHCl solution) is shown in FIG. 25.
(4) IR spectrum (KBr) is shown in FIG. 26.

The spectrum shows an absorption due to ester C=O stretching vibration near 1700 cm$^{-1}$.

APPLICATION EXAMPLE 3

[Synthesis of tetrakis(n-amyloxycarbonyl) zinc naphthalocyanine]

1.46 Grams (5 mmols) of 6-(n-amyloxycarbonyl)-2,3-dicyanonaphthalene, 105 mg (1.6 mmols) of powdered zinc, 10 mg of ammonium molybdate and 5 g of urea were reacted with one another with sufficient stirring at 220° C. for about 2.5 hours. After cooling, the reaction mixture was treated in the same manner as in Application Example 1 to obtain 937 mg of black crystals. The crystals were identified as tetrakis(n-amyloxycarbonyl) zinc naphthalocyanine from the following analysis results:

(1) Melting point >300° C.

| (2) Elementary analysis values: | | | |
|---|---|---|---|
| | C | H | N |
| Calculated (%) | 70.04 | 5.22 | 9.08 |
| Found (%) | 69.35 | 5.22 | 9.08 |

Figure 27:
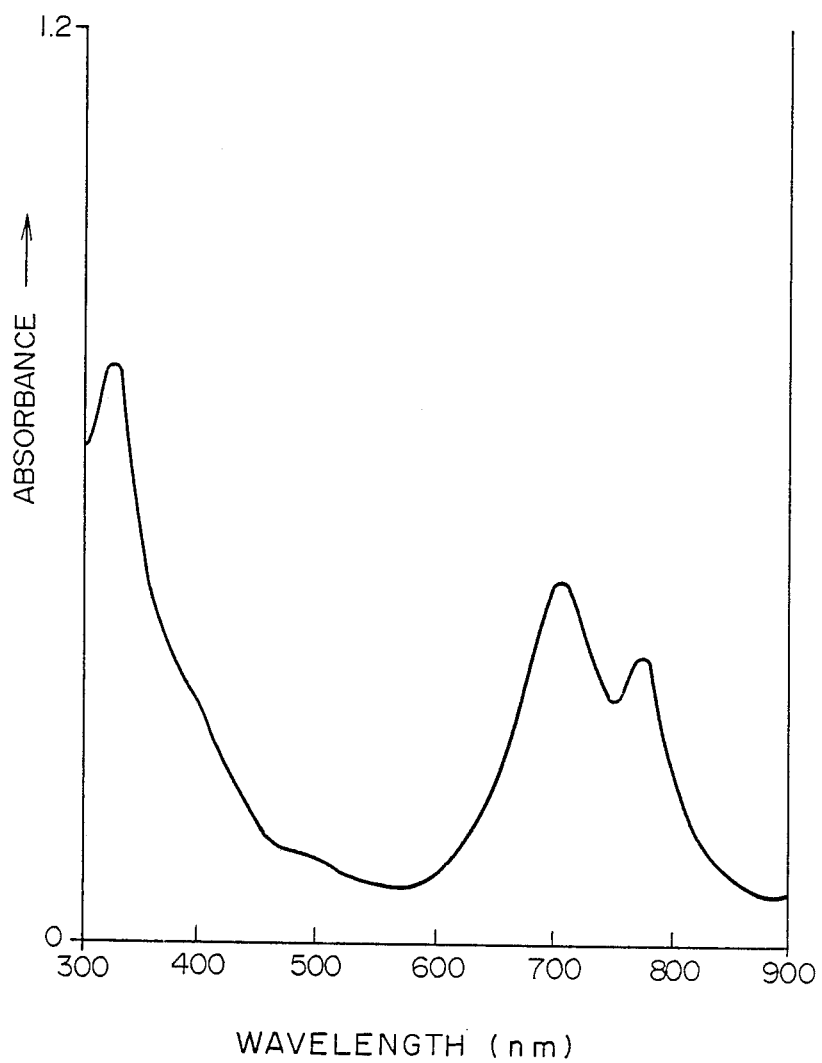
FIG. 27 is an electronic spectrum of tetrakis(n-amyloxycarbonyl) zinc naphthalocyanine.
Figure 28:
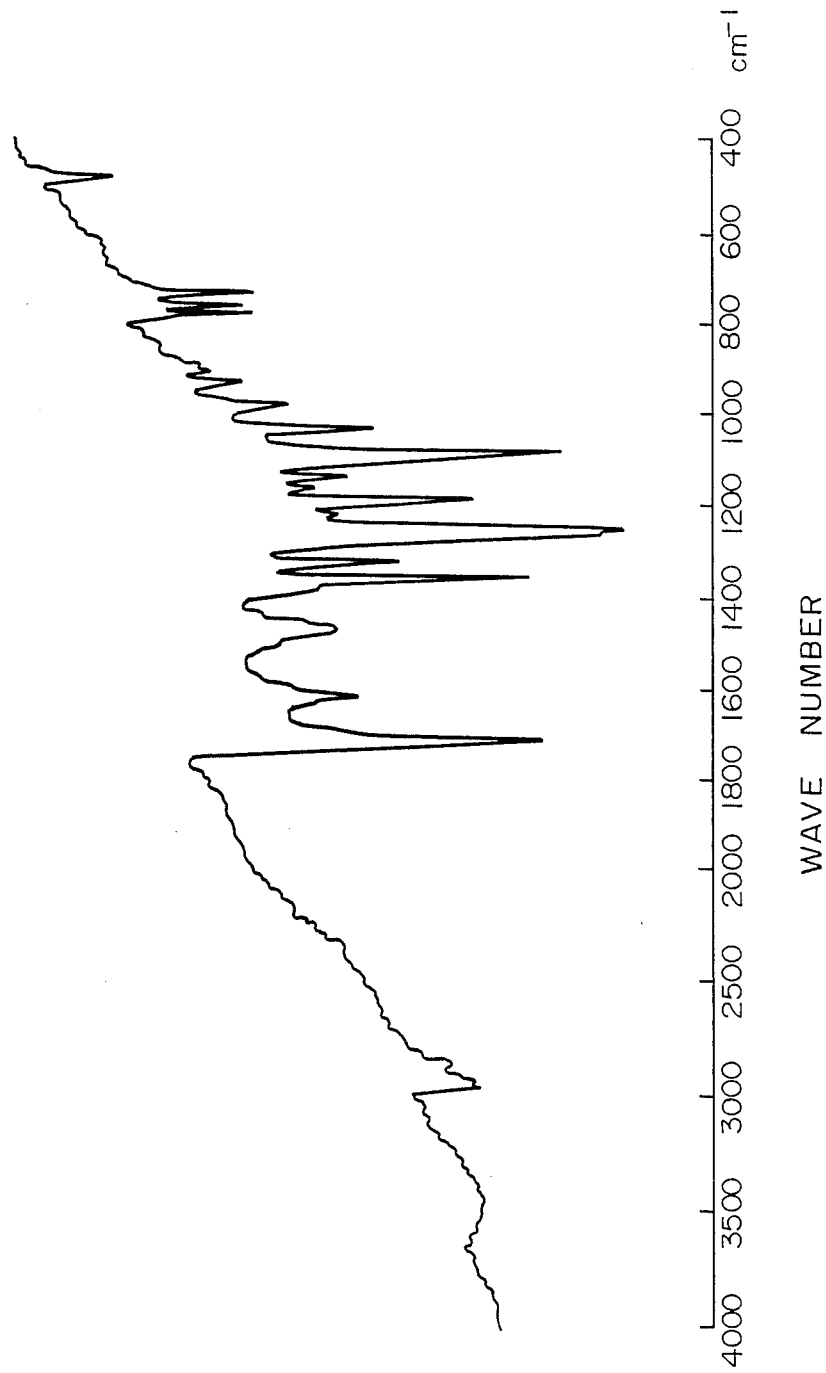
FIG. 28 is an IR spectrum of tetrakis(n-amyloxycarbonyl) zinc naphthalocyanine.

(3) Electronic spectrum (CHCl$_3$ solution) is shown in FIG. 27.
(4) IR spectrum (KBr) is shown in FIG. 28.

The spectrum shows an absorption due to ester C=O stretching vibration near 1700 cm$^{-1}$.

APPLICATION EXAMPLE 4

[Synthesis of tetrakis(n-octyloxycarbonyl) vanadyl naphthalocyanine]

1.67 Grams (5 mmols) of 6-(n-octyloxycarbonyl)-2,3-dicyanonaphthalene, 0.32 g (1.6 mmols) of vanadium trichloride, 10 mg of ammonium molybdate and 5 g of urea were reacted with one another with sufficient stirring at about 220° C. for about 2.5 hours. After cooling, the reaction mixture was treated in the same manner as in Application Example 1 to obtain 1.33 g of black crystals. The crystals were identified as tetrakis(n-octyloxycarbonyl) vanadyl naphthalocyanine from the following analysis results:

(1) Melting point >300° C.

| (2) Elementary analysis values: | | | |
|---|---|---|---|
| | C | H | N |
| Calculated (%) | 71.83 | 6.31 | 7.98 |
| Found (%) | 71.99 | 6.18 | 8.29 |

Figure 29:
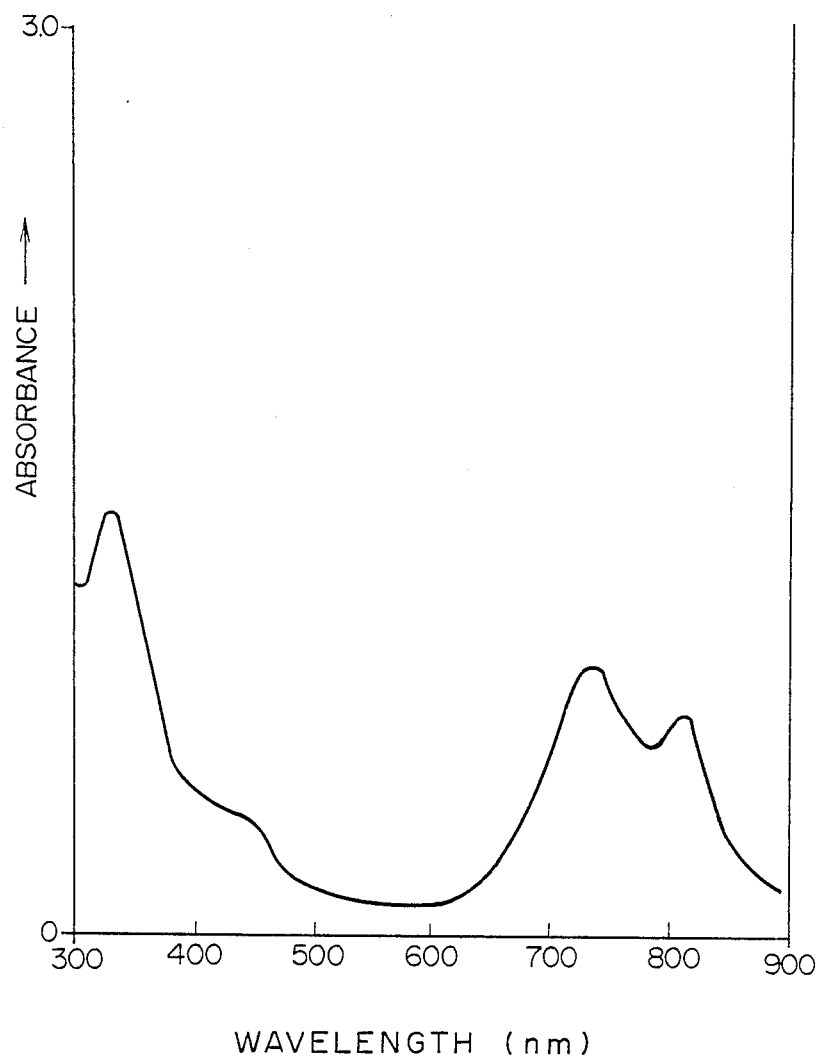
FIG. 29 is an electronic spectrum of tetrakis(n-octyloxycarbonyl) vanadyl naphthalocyanine.
Figure 30:
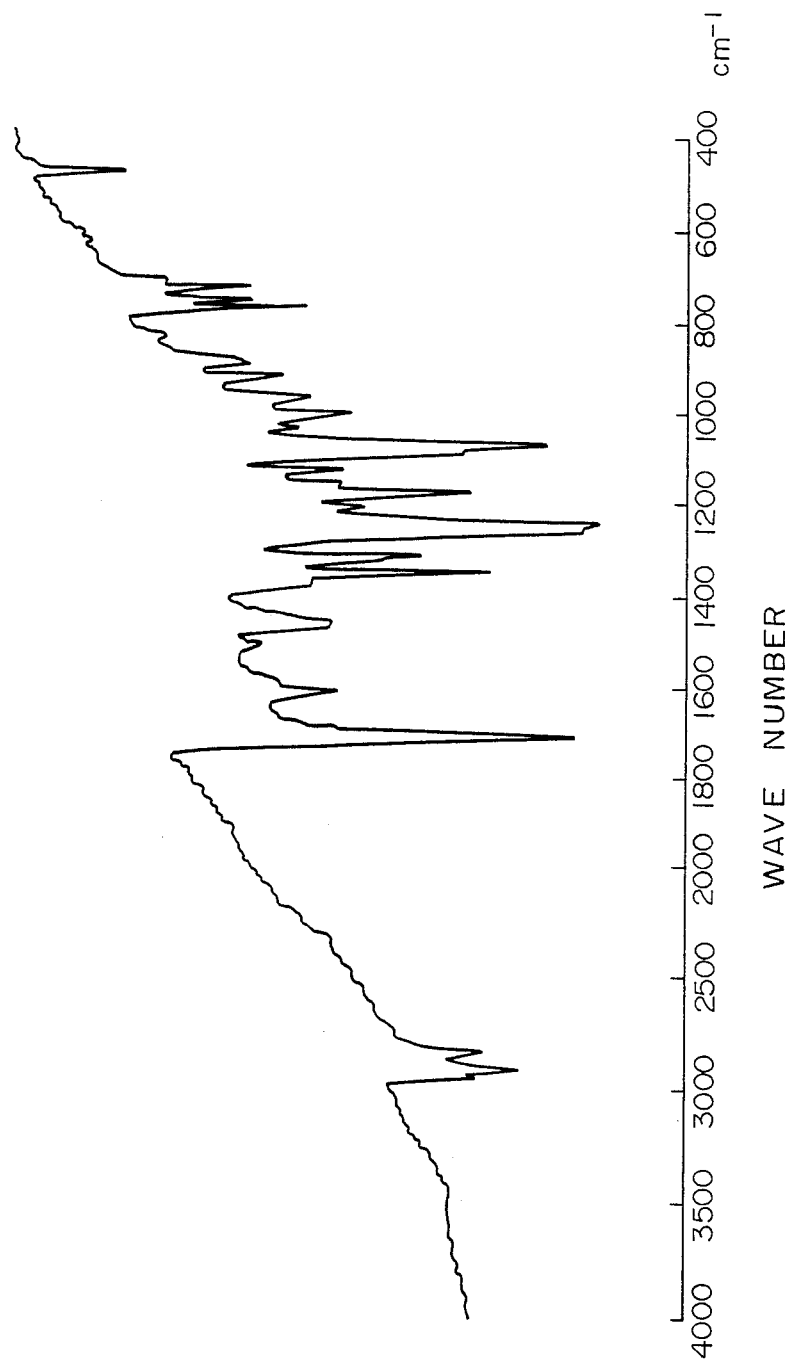
FIG. 30 is an IR spectrum of tetrakis(n-octyloxycarbonyl) vanadyl naphthalocyanine.

(3) Electronic spectrum (CHCl$_3$ solution) is shown in FIG. 29.
(4) IR spectrum (KBr) is shown in FIG. 30.

The spectrum shows an absorption due to ester C=O stretching vibration near 1700 cm$^{-1}$.

APPLICATION EXAMPLE 5

[Synthesis of tetrakis(n-octyloxycarbonyl) copper naphthalocyanine]

1.67 Grams (5 mmols) of 6-(n-octyloxycarbonyl)-2,3-dicyanonaphthalene, 273 mg (1.6 mmols) of cupric chloride dihydrate, 10 mg of ammonium molybdate and 5 g of urea were reacted with one another with sufficient stirring at about 220° C. for about 2.5 hours. After cooling the reaction mixture was treated in the same manner as in Application Example 1 to obtain 1.39 g of black crystals. The crystals were identified as tetrakis(n-octyloxycarbonyl) copper naphthalocyanine from the following analysis results:

(1) Melting point >300° C.

| (2) Elementary analysis values: | | | |
|---|---|---|---|
| | C | H | N |
| Calculated (%) | 72.00 | 6.33 | 8.00 |
| Found (%) | 71.95 | 6.08 | 8.14 |

Figure 31:
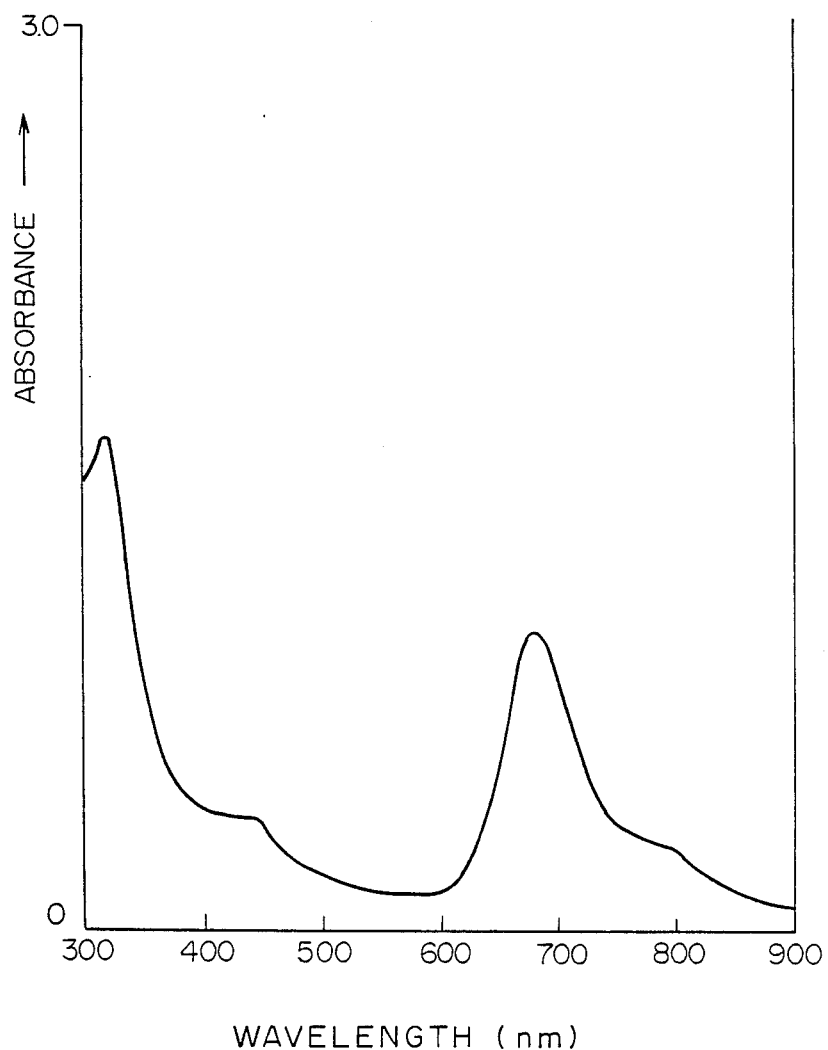
FIG. 31 is an electronic spectrum of tetrakis(n-octyloxycarbonyl) copper naphthalocyanine.
Figure 32:
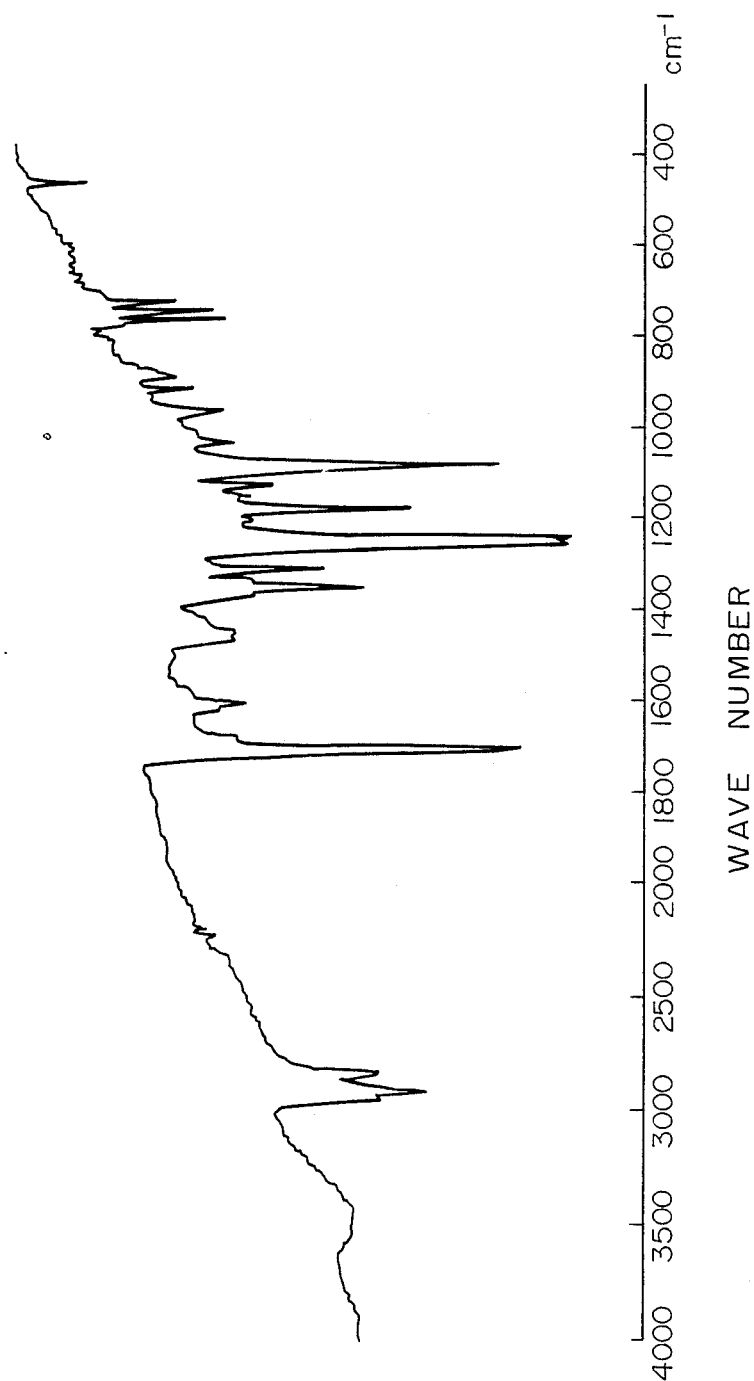
FIG. 32 is an IR spectrum of tetrakis(n-octyloxycarbonyl) copper naphthalocyanine.

(3) Electronic spectrum (CHCl$_3$ solution) is shown in FIG. 31.
(4) IR spectrum (KBr) is shown in FIG. 32.

The spectrum shows an absorption due to ester C=O stretching vibration near 1700 cm$^{-1}$.

APPLICATION EXAMPLE 6

[Synthesis of tetrakis(n-tetradecyloxycarbonyl) vanadyl naphthalocyanine]

42 Milligrams (0.1 mmol) of 6-(n-tetradecyloxycarbonyl)-2,3-dicyanonaphthalene, 6 mg (4.0×10$^{-2}$ mmol) of vanadium trichloride, 0.2 mg of ammonium molybdate and 100 mg of urea were reacted with one another with sufficient stirring at about 220° C. for about 2.5 hours. After cooling the reaction mixture was treated in the same manner as in Application Example 1 to obtain 21 mg of black crystals. The crystals were identified as tetrakis-(n-tetradecyloxycarbonyl) vanadyl naphthalocyanine from the following analysis results:

(1) Softening point: 210°-212° C.

| (2) Elementary analysis values: | | | |
|---|---|---|---|
| | C | H | N |
| Calculated (%) | 74.50 | 7.87 | 6.44 |
| Found (%) | 74.66 | 7.96 | 6.32 |

Figure 33:
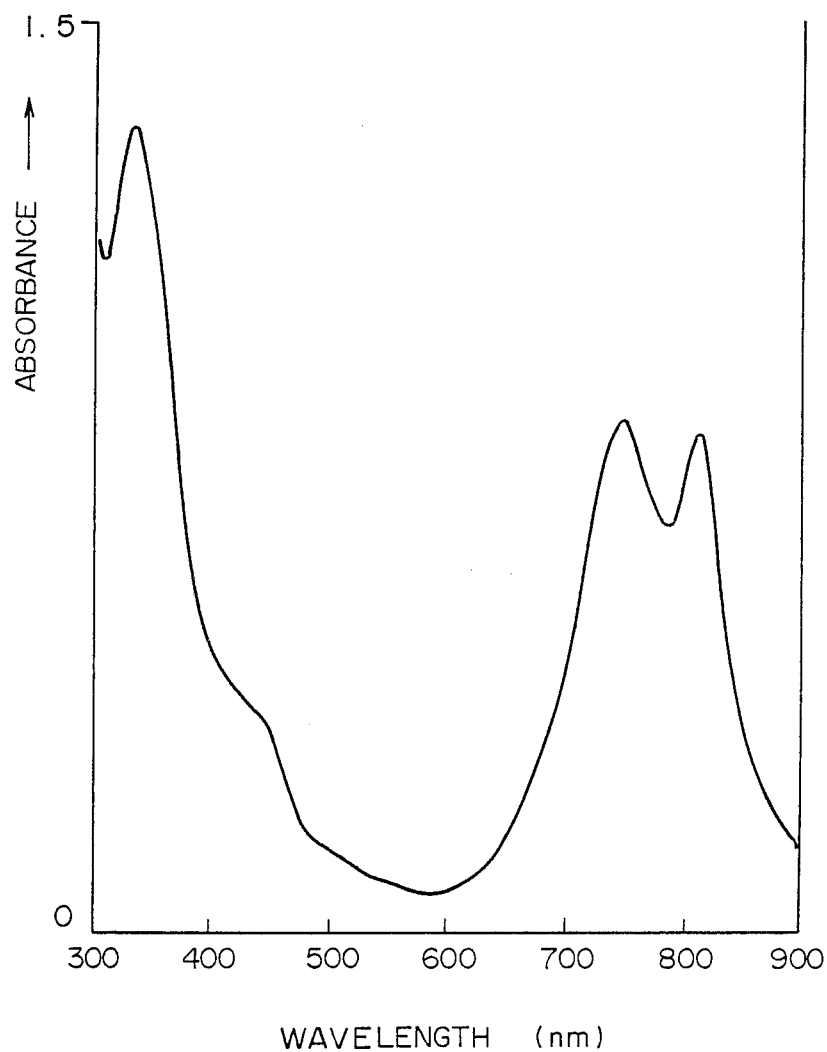
FIG. 33 is an electronic spectrum of tetrakis(n-tetradecyloxycarbonyl) vanadyl naphthalocyanine.

(3) Electronic spectrum (CHCl$_3$ solvent) is shown in FIG. 33.

Figure 34:
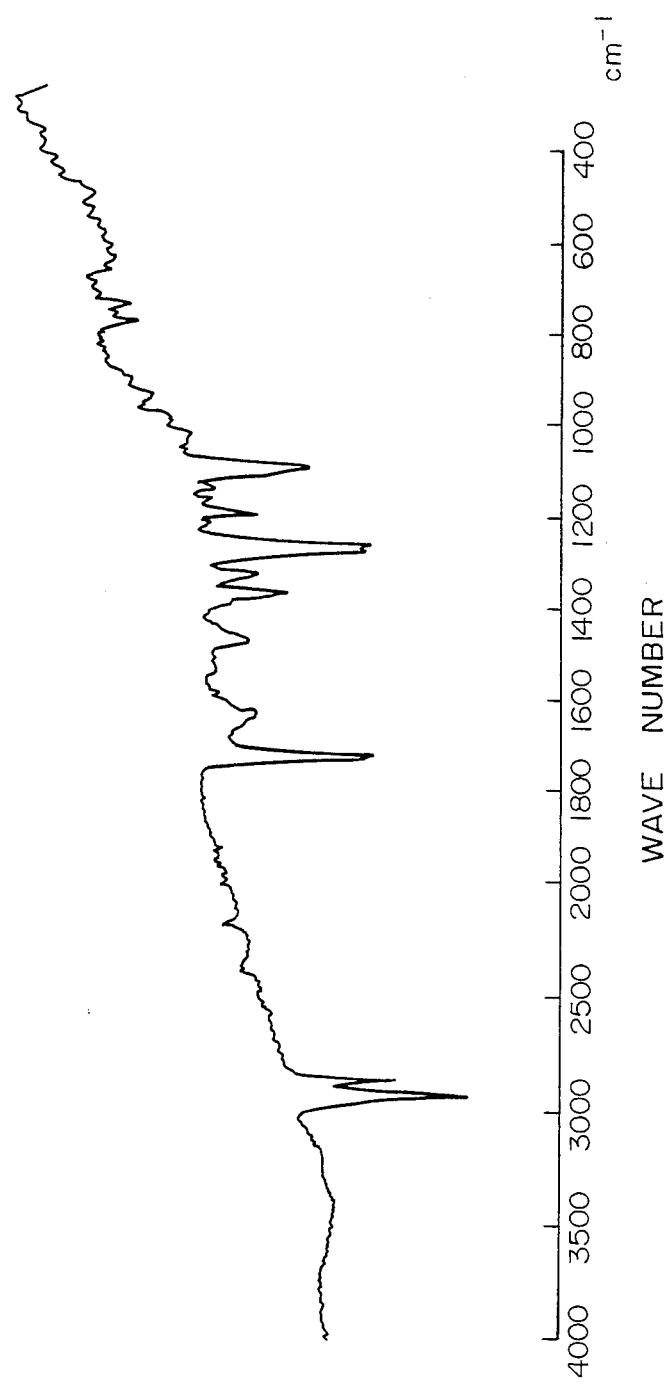
FIG. 34 is an IR spectrum of tetrakis(n-tetradecyloxycarbonyl) vanadyl naphthalocyanine.

(4) IR spectrum (KBr) is shown in FIG. 34
The spectrum shows an absorption due to ester C=O stretching vibration near 1720 cm$^{-1}$.

APPLICATION EXAMPLE 7

[Synthesis of tetrakis(n-tetradecyloxycarbonyl) copper naphthalocyanine]

42 Milligrams (0.1 mmol) of 6-(n-tetradecyloxycarbonyl)-2,3-dicyanonaphthalene, 5 mg ($3.2 \times 10^{-2}$ mmol) of cupric chloride dihydrate, 0.2 mg of ammonium molybdate and 100 mg of urea were reacted with one another with sufficient stirring at about 220° C. for about 2.5 hours. After cooling the reaction mixture was treated in the same manner as in Application Example 1 to obtain 21 mg of black crystals. The crystals were identified as tetrakis(n-tetradecyloxycarbonyl) copper naphthalocyanine form the following analysis results:

(1) Softening point: 168°–171° C.

| (2) Elementary analysis values: | | | |
|---|---|---|---|
| | C | H | N |
| Calculated (%) | 74.64 | 7.89 | 6.45 |
| Found (%) | 74.82 | 7.76 | 6.37 |

Figure 35:
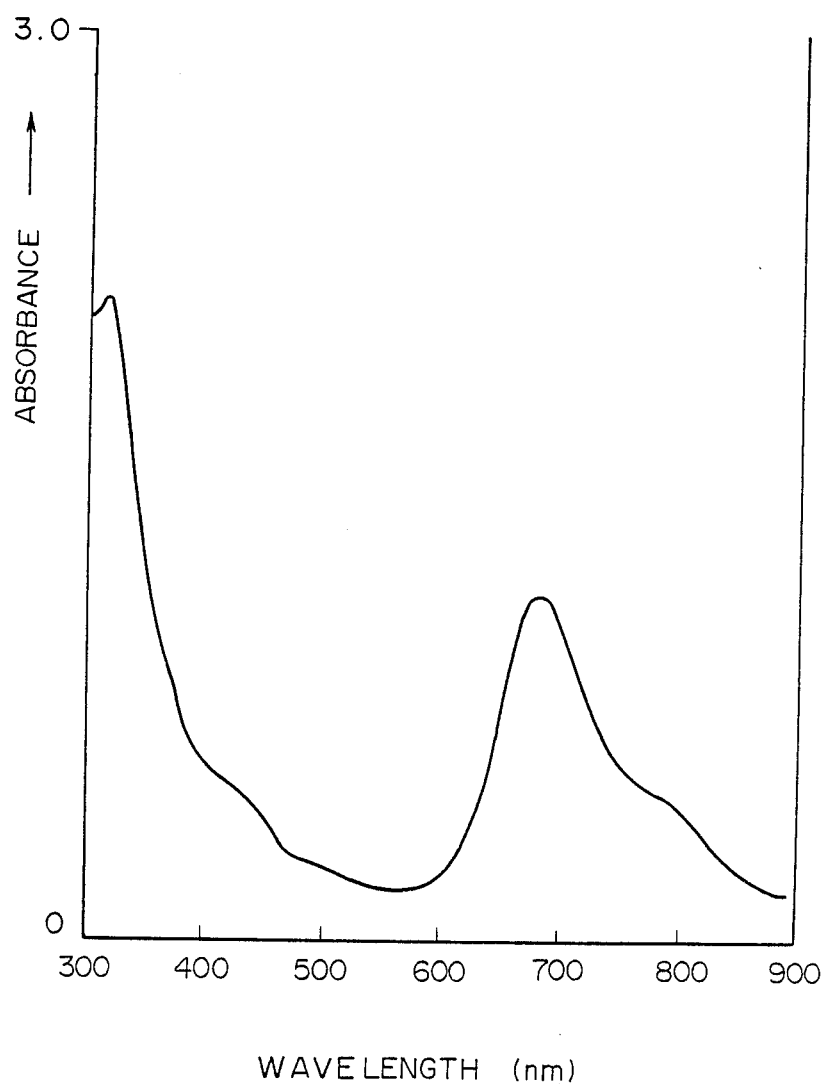
FIG. 35 is an electronic spectrum of tetrakis(n-tetradecyloxycarbonyl) copper naphthalocyanine.

(3) Electronic spectrum (CHCl$_3$ solvent) is shown in FIG. 35.

Figure 36:
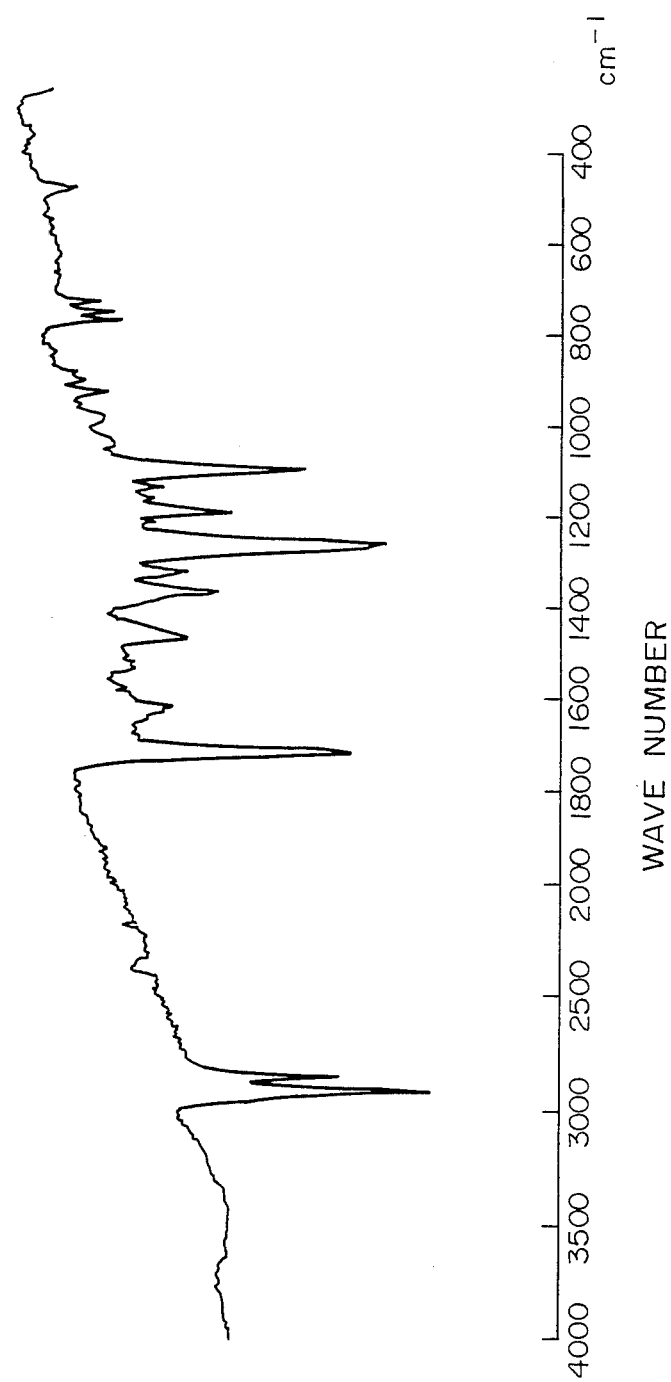
FIG. 36 is an IR spectrum of tetrakis(n-tetradecyloxycarbonyl) copper naphthalocyanine.

(4) IR spectrum (KBr) is shown in FIG. 36.

The spectrum shows an absorption due to ester C=O stretching vibration near 1720 cm$^{-1}$.

APPLICATION EXAMPLE 8

[Synthesis of tetrakis(n-hexadecyloxycarbonyl) vanadyl naphthalocyanine]

45 Milligrams (0.1 mmol) of 6-(n-hexadecyloxy carbonyl)-2,3-dicyanonaphthalene, 6 mg ($4.0 \times 10^{-2}$ mmol) of vanadium trichloride, 0.2 mg of ammonium molybdate and 100 mg of urea were reacted with one another with sufficient stirring at about 220° C. for about 2.5 hours. After cooling, the reaction mixture was treated in the same manner as in Application Example 1 to obtain 13 mg of black crystals. The crystals were identified as tetrakis-(n-hexadecyloxycarbonyl) vanadyl naphthalocyanine from the following analysis results:

(1) Softening point: 151°–154° C.

| (2) Elementary analysis values: | | | |
|---|---|---|---|
| | C | H | N |
| Calculated (%) | 75.17 | 8.27 | 6.05 |
| Found (%) | 75.26 | 8.19 | 6.13 |

Figure 37:
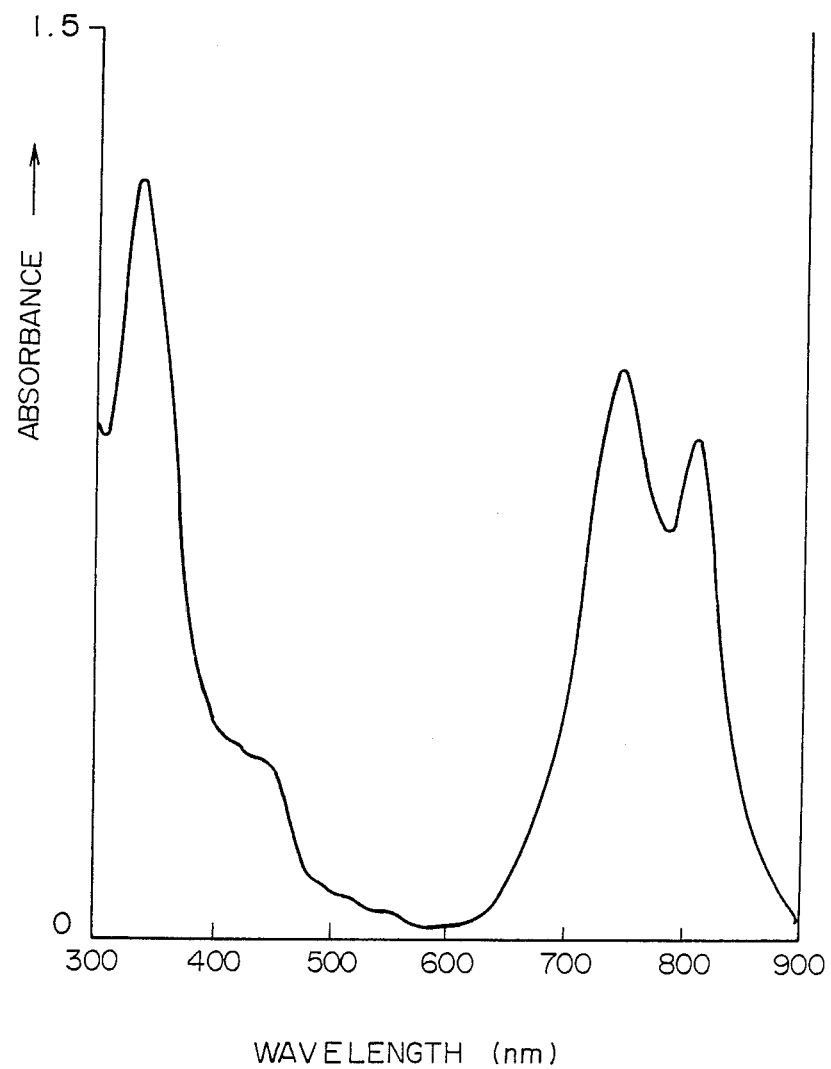
FIG. 37 is an electronic spectrum of tetrakis(n-hexadecyloxycarbonyl) vanadyl naphthalocyanine.

(3) Electronic spectrum (CHCl$_3$ solvent) is shown in FIG. 37.

Figure 38:
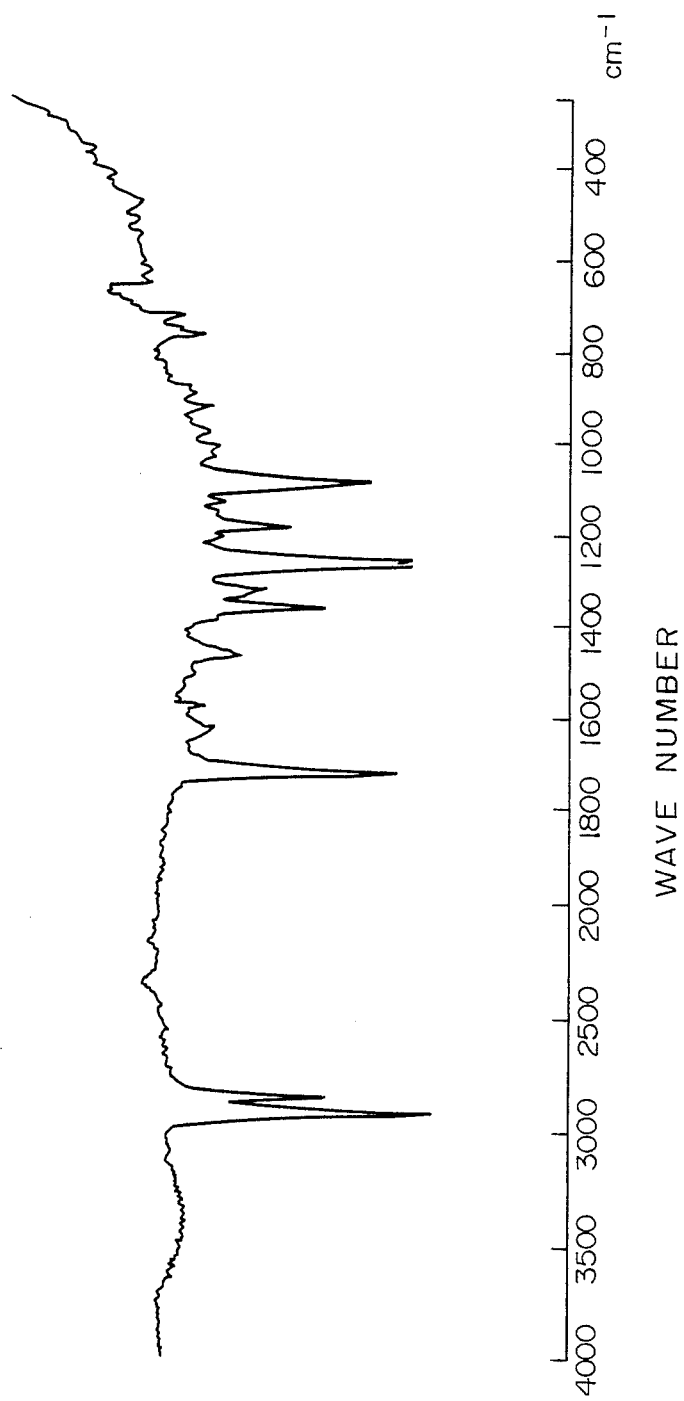
FIG. 38 is an IR spectrum of tetrakis-(n-hexadecyloxycarbonyl) vanadyl naphthalocyanine.

(4) IR spectrum (KBr) is shown in FIG. 38.

The spectrum shows an absorption due to ester C=O stretching vibration near 1720 cm$^{-1}$.

APPLICATION EXAMPLE 9

[Synthesis of tetrakis(n-octadecyloxycarbonyl) copper naphthalocyanine [exemplified compound (12)]

200 Milligrams (0.42 mmol) of 6-(n-octadecyloxycarbonyl)-2,3-dicyanonaphthalene, 23 mg (0.13 mmol) of cupric chloride dihydrate, 1 mg of ammonium molybdate and 0.42 g of urea were reacted with one another with sufficient stirring at about 220° C. for about 2.5 hours. After cooling, the reaction mixture was treated in the same manner as in Application Example 1 to obtain 160 mg of tetrakis(n-octadecyloxycarbonyl) copper naphthalocyanine in the form of dark-green crystals. The crystals were identified as tetrakis(n-octadecyloxycarbonyl) copper naphthalocyanine from the following analysis results:

(1) Softening point: 119°–121° C.

| (2) Elementary analysis values: | | | |
|---|---|---|---|
| | C | H | N |
| Calculated (%) | 75.90 | 8.63 | 5.71 |
| Found (%) | 75.63 | 8.51 | 5.66 |

Figure 39:
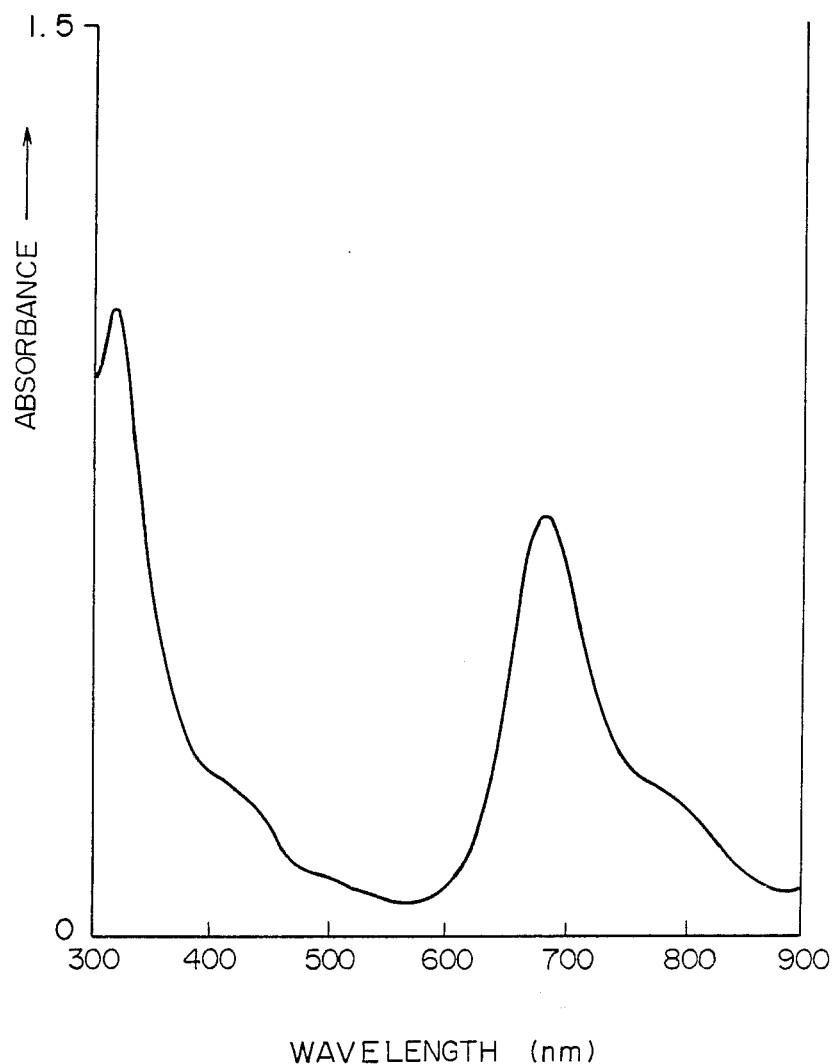
FIG. 39 is an electronic spectrum of tetrakis(n-octadecyloxycarbonyl) copper naphthalocyanine.

(3) Electronic spectrum (CHCl$_3$ solution) is shown in FIG. 39.

Figure 40:
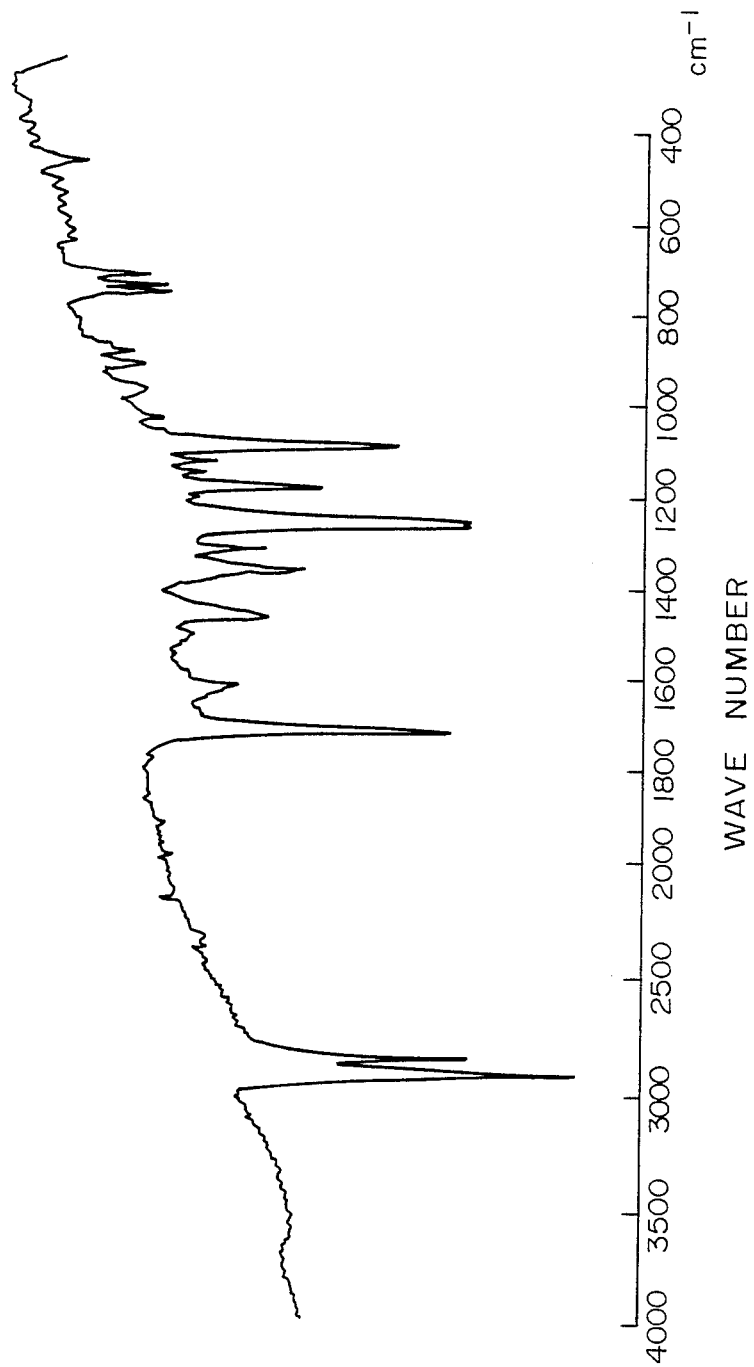
FIG. 40 is an IR spectrum of tetrakis(n-octadecyloxycarbonyl) copper naphthalocyanine.

(4) IR spectrum (KBr) is shown in FIG. 40.

The spectrum shows an absorption due to ester C=O stretching vibration near 1720 cm$^{-1}$.

APPLICATION EXAMPLE 10

[Synthesis of tetrakis(n-eicosyloxycarbonyl) vanadyl naphthalocyanine]

52 Milligrams (0.1 mmol) of 6-(n-eicosyloxycarbonyl)-2,3-dicyanonaphthalene, 6 mg ($4.0 \times 10^{-2}$ mmol) of vanadium trichloride, 0.2 mg of ammonium molybdate and 100 mg of urea were reacted with one another with sufficient stirring at about 220° C. for about 2.5 hours. After cooling, the reaction mixture was treated in the same manner as in Application Example 1 to obtain 26 mg of black crystals. The crystals were identified as tetrakis(n-eicosyloxycarbonyl) vanadyl naphthalocyanine from the following analysis results:

(1) Softening point: 83°–85° C.

| (2) Elementary analysis values: | | | |
|---|---|---|---|
| | C | H | N |
| Calculated (%) | 76.30 | 8.93 | 5.39 |
| Found (%) | 76.92 | 8.87 | 5.28 |

Figure 41:
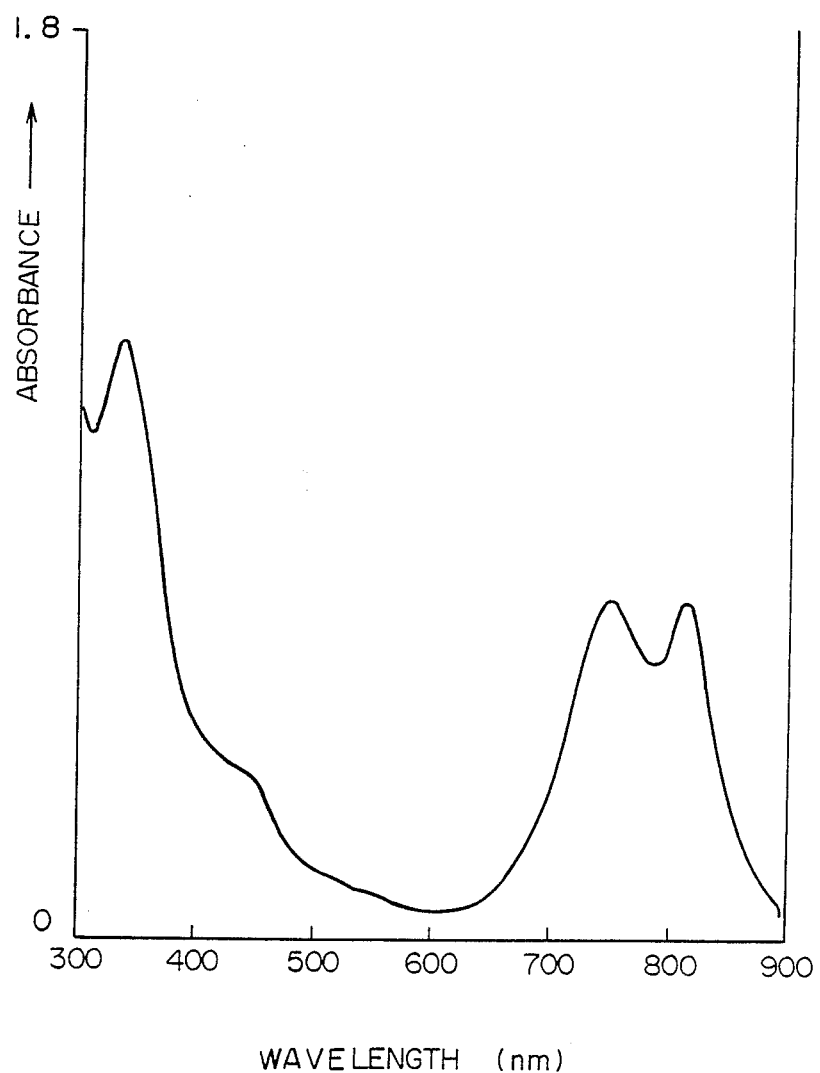
FIG. 41 is an electronic spectrum of tetrakis(n-eicosyloxycarbonyl) vanadyl naphthalocyanine.

(3) Electronic spectrum (CHCl$_3$ solvent) is shown in FIG. 41.

Figure 42:
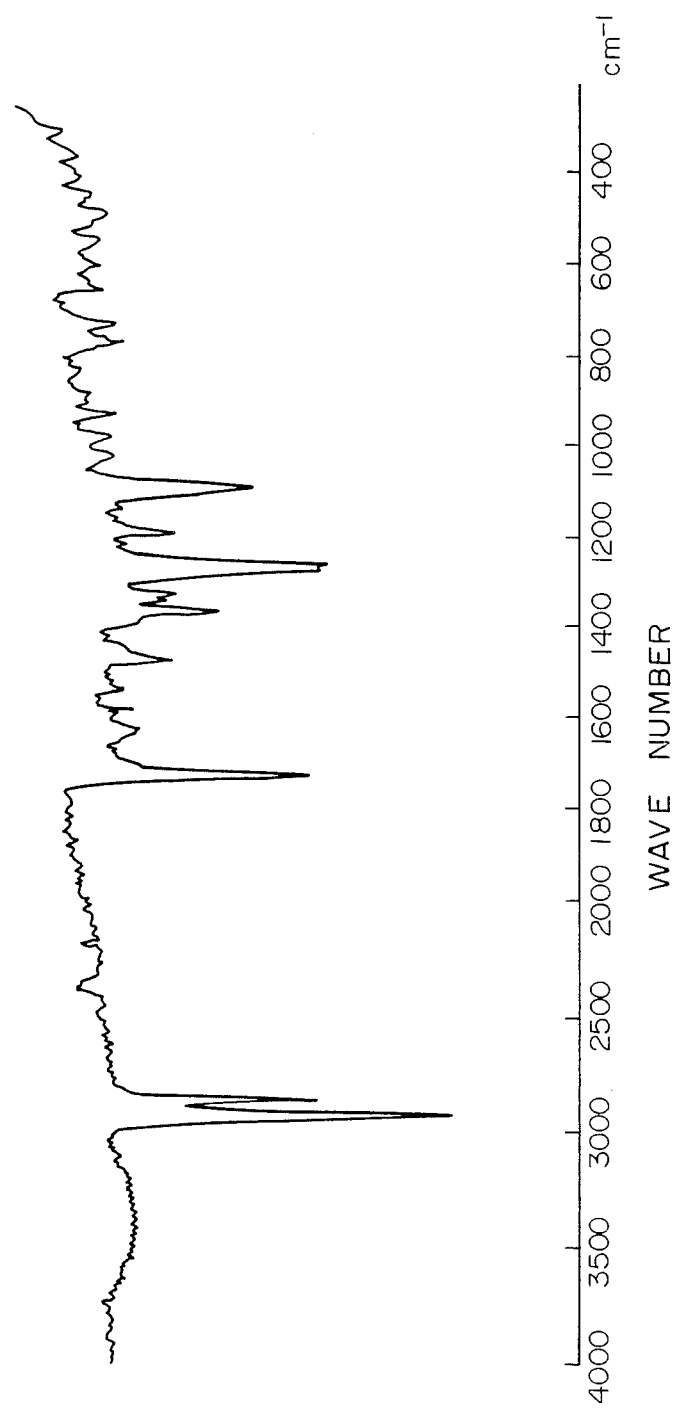
FIG. 42 is an IR spectrum of tetrakis-(n-eicosyloxycarbonyl) vanadyl naphthalocyanine.

(4) IR spectrum (KBr) is shown in FIG. 42.

The spectrum shows an absorption due to ester C=O stretching vibration near 1720 cm$^{-1}$.

APPLICATION EXAMPLE 11

[Synthesis of tetrakis(n-eicosyloxycarbonyl) copper naphthalocyanine]

52 Milligrams (0.1 mmol) of 6-(n-eicosyloxycarbonyl)-2,3-dicyanonaphthalene, 5 mg ($3.2 \times 10^{-2}$ mmol) of cupric chloride dihydrate, 0.2 mg of ammonium molybdate and 100 mg of urea were reacted with one another with sufficient stirring a about 220° C. for about 2.5 hours. After being allowed to cool, the reaction mixture was treated in the same manner as in Application Example 1 to obtain 36 mg of black crystals. The crystals were identified as tetrakis(n-eicosyloxycarbonyl) copper naphthalocyanine from the following analysis results:

(1) Softening point: 67°–70° C.

| (2) Elementary analysis values: | | | |
|---|---|---|---|
| | C | H | N |
| Calculated (%) | 76.43 | 8.94 | 5.40 |

-continued

| (2) Elementary analysis values: | | | |
|---|---|---|---|
| | C | H | N |
| Found (%) | 76.62 | 8.78 | 5.61 |

Figure 43:
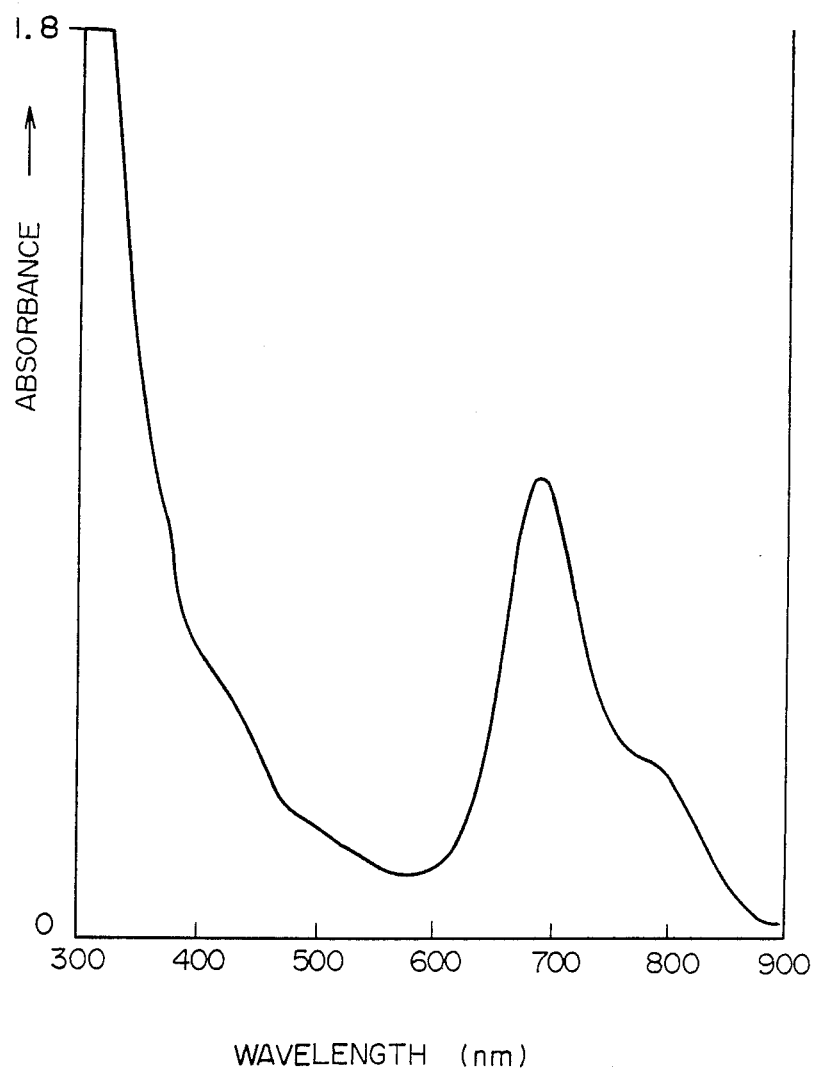
FIG. 43 is an electronic spectrum of tetrakis(n-eicosyloxycarbonyl) copper naphthalocyanine.

(3) Electronic spectrum (CHCl$_3$ solvent) is shown in FIG. 43.

Figure 44:
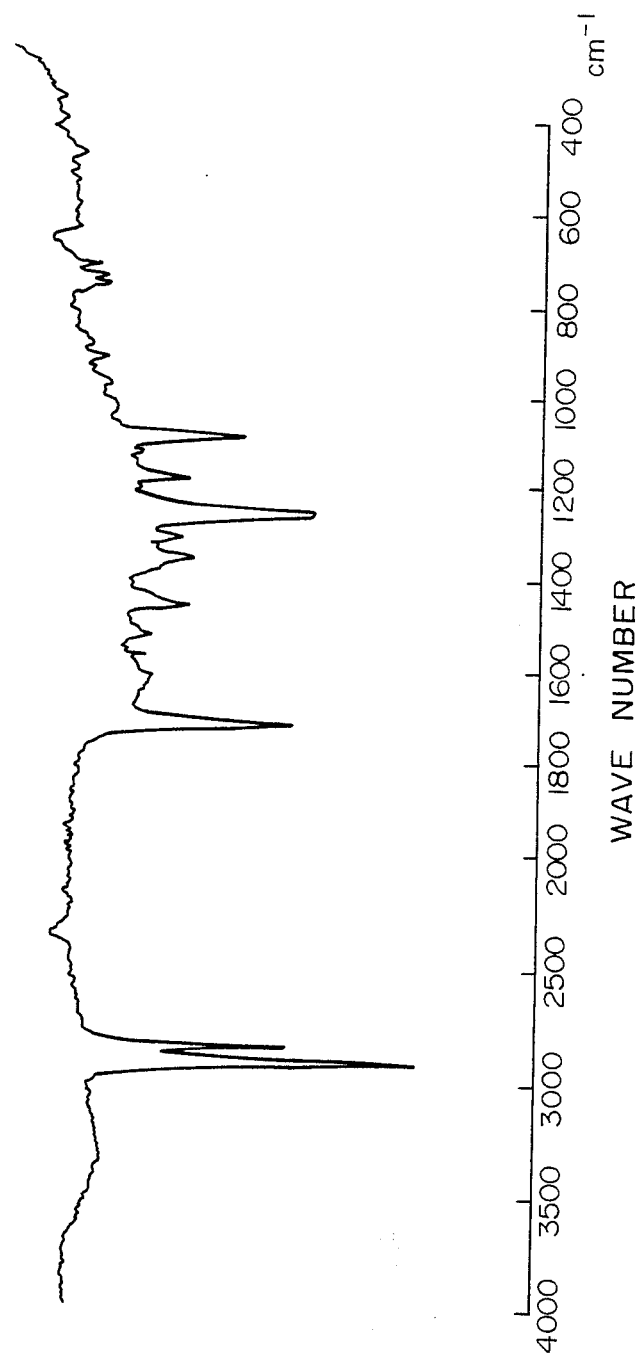
FIG. 44 is an IR spectrum of tetrakis(n-eicosyloxycabonyl) copper naphthalocyanine.

(4) IR spectrum (KBr) is shown in FIG. 44.

The spectrum shows an absorption due to ester C=O stretching vibration near 1720 cm$^{-1}$.

APPLICATION EXAMPLE 12

[Synthesis of tetrakis(n-octadecyloxycarbonyl) vanadyl naphthalocyanine]

650 Milligrams (1.37 mmols) of 6-(n-octadecyloxycarbonyl)-2,3-dicyanonaphthalene, 88 mg (1.6 mmols) of vanadium trichloride, 3 mg of ammonium molybdate and 1.37 g of urea were reacted with one another with sufficient stirring at about 220° C. for about 2.5 hours. After cooling, the reaction mixture was treated in the same manner as in Application Example 1 to obtain 556 mg of tetrakis(n-octadecyloxycarbonyl) vanadyl naphthalocyanine in the form of black crystals. The crystals were identified as tetrakis(n-octadecyloxycarbonyl) vanadyl naphthalocyanine from the following analysis results:

(1) Softening point: 135°-138° C.

| (2) Elementary analysis values: | | | |
|---|---|---|---|
| | C | H | N |
| Calculated (%) | 75.77 | 8.61 | 5.70 |
| Found (%) | 75.25 | 8.51 | 6.17 |

Figure 45:
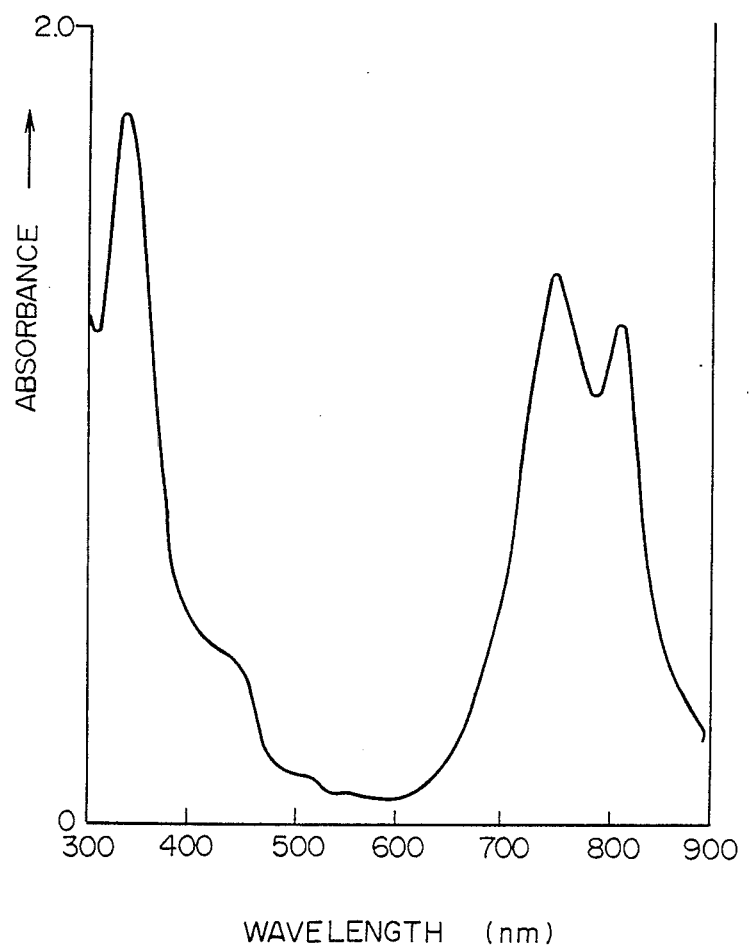
FIG. 45 is an electronic spectrum of tetrakis(n-octadecyloxycarbonyl) vanadyl naphthalocyanine.

(3) Electronic spectrum (CHCl$_3$ solution) is shown in FIG. 45.

Figure 46:
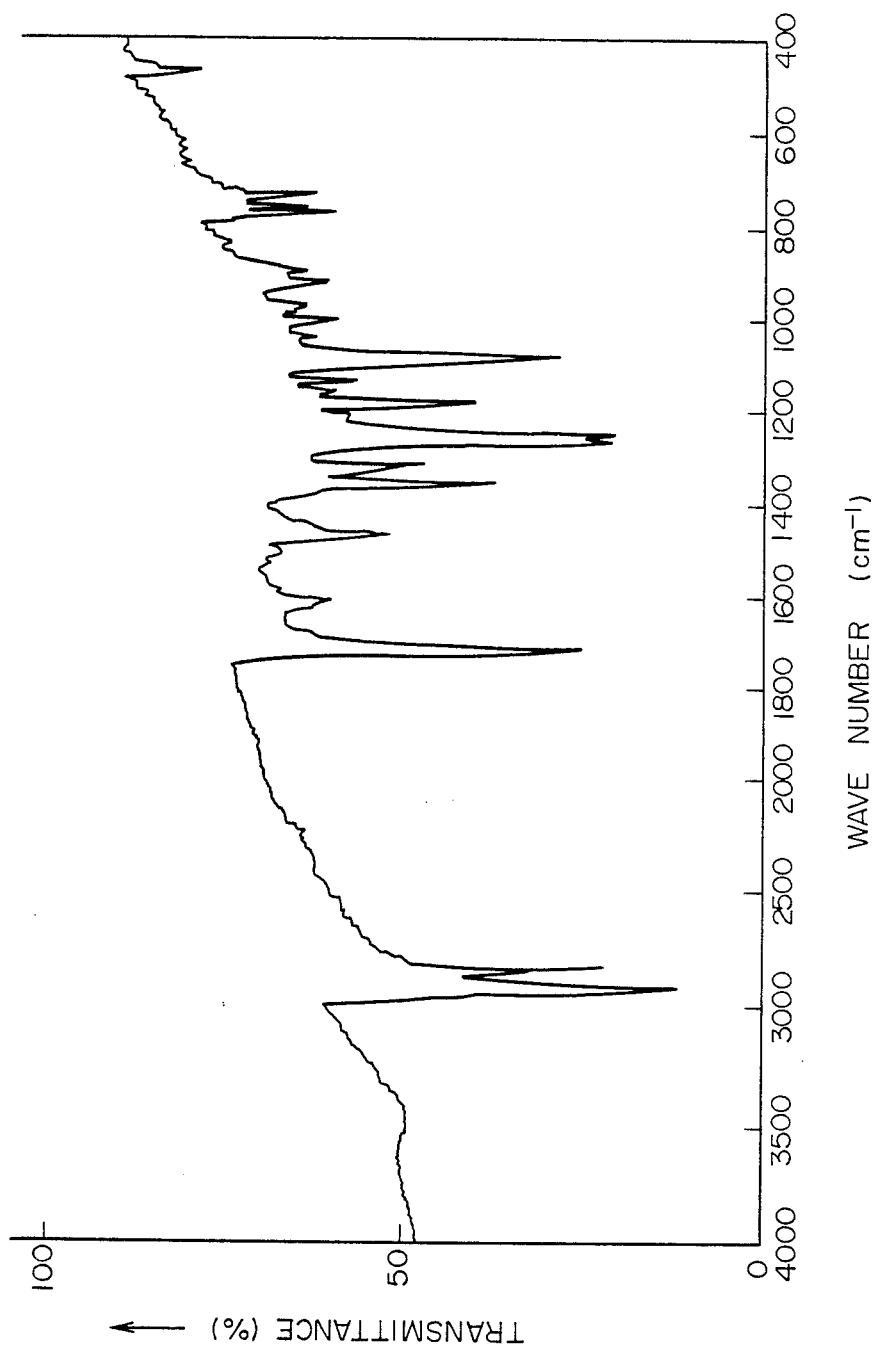
FIG. 46 is an IR spectrum of tetrakis(n-octadecyloxycarbonyl) vanadyl naphthalocyanine.

(4) IR spectrum (KBr) is shown in FIG. 46.

The spectrum shows an absorption due to ester C=O stretching vibration near 1700 cm$^{-1}$.

TEST EXAMPLE 1

With 2.5 g of tetrakis(n-octyloxycarbonyl) vanadyl naphthalocyanine were blended 5.0 g of silicone resin (KR 255, a trade name, mfd. by Shin-etsu Chemical Industry Co., Ltd.) and 92.5 g of tetrahydrofuran, and the resulting solution was kneaded in a ball mill (a 10-cm pot mill mfd. by Nippon Kagaku Togyo Co., Ltd.) for 5 hours. The pigment dispersion thus obtained was coated on an aluminum plate (an electric conductor) by means of an applicator and dried at 90° C. for 40 minutes to form a charge generating material layer of 1 μm in thickness.

Next, 10 g of dimethylamino(o-ethoxy)benzaldehyde diphenylhydrazone as charge transport material, 10 g of polycarbonate resin (Iupilon S-2000, mfd. by Mitsubishi Gas-Chemical Co., Inc.) as binder, 40 g of methylene chloride and 40 g of 1,1,2-trichloroethane were made into a homogeneous solution, which was then coated on the above-mentioned charge generating material layer by means of an applicator and dried at 90° C. for 40 minutes to form a charge transport material layer of 15 um in thickness, whereby an electrophotographic plate was obtained.

Electrophotographic characteristics of the electrophotographic plate thus produced were measured by means of an electrostatic recording paper analyzer (SP-428, a trade name, mfd. by Kawaguchi Electric Works Co., Ltd.). In this case, the electrophotographic plate was charge-accepted by corona electrical charging at negative 5 KV for 10 seconds, allowed to stand in the dark for 30 seconds, and then exposed to light from a tungsten lamp to adjust the luminance on its surface to 2 lux. The decay of the surface potential and time in this case were measured, and the sensitivity was evaluated in terms of the product of the time t (second) required for the surface potential before the light irradiation to be reduced by on half and the luminance (lux). Consequently, a high sensitivity of 3.0 lux.second was attained.

TEST EXAMPLE 2

An electrophotographic plate was produced in the same manner as in Test Example 1, except that tetrakis(n-octyloxycarbonyl) copper naphthalocyanine was used in place of tetrakis(n-octyloxycarbonyl) vanadyl naphthalocyanine. Its sensitivity was measured in the same manner as in Test Example 1 to obtain a good result of 2.3 lux. second.

TEST EXAMPLE 3

An electrophotographic plate was produced in the same manner as in Test Example 1, except that tetrakis(n-amyloxycarbonyl) vanadyl naphthalocyanine was used in place of tetrakis(n-octyloxycarbonyl) vanadyl naphthalocyanine. Its sensitivity was measured in the same manner as in Test Example 1 to obtain a good result of 2.8 lux. second.

TEST EXAMPLE 4

An electrophotographic plate was produced in the same manner as in Test Example 1, except that tetrakis(n-amyloxycarbonyl) copper naphthalocyanine was used in place of tetrakis(n-octyloxycarbonyl) vanadyl naphthalocyanine. Its sensitivity was measured in the same manner as in Test Example 1 to obtain a good result of 2.1 lux.second.

TEST EXAMPLE 5

An electrophotographic plate was produced in the same manner as in Test Example 1, except that tetrakis-(n-amyloxycarbonyl) zinc naphthalocyanine was used in place of tetrakis(n-octyloxycarbonyl) vanadyl naphthalocyanine. Its sensitivity was measured in the same manner as in Text Example 1 to obtain a good result of 2.6 lux.second.

The 5- or 6-(alkoxycarbonyl)-2,3-dicyanonaphthalene of the formula (I) of this invention is a novel compound, and by reacting this compound with various metals or metal salts, tetrakis(alkoxycarbonyl) metal naphthalocyanines having an absorption at a desired position between about 600 nm and about 850 nm can be synthesized in high yield. The tetrakis(alkoxycarbonyl) metal naphthalocyanines are soluble in aromatic and halogenated solvents, can easily be purified, and can be obtained in high purity. Furthermore, the tetrakis(alkoxycarbonyl) metal-naphthalocyanines are very excellent in ability to absorb visible to near infrared rays when the metal is properly selected, and therefore they are useful as electrophotographic photosensitive materials, etc.

What is claimed is:

1. A 5- or 6-alkoxycarbonyl-2,3-dicyanonaphthalene represented by the formula:

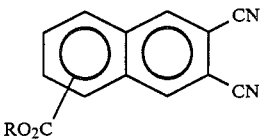

wherein R is an alkyl group having 1 to 22 carbon atoms.

2. A 5- or 6-alkoxycarbonyl-2,3-dicyanonaphthalene according to claim 1, which is 6-methoxycarbonyl-2,3-dicyanonaphthalene.

3. A 5- or 6-alkoxycarbonyl-2,3-dicyanonaphthalene according to claim 1, which is 6-(n-amyloxycarbonyl)-2,3-dicyanonaphthalene.

4. A 5- or 6-alkoxycarbonyl-2,3-dicyanonaphthalene according to claim 1, which is 6-(n-octyloxycarbonyl)-2,3-dicyanonaphthalene.

5. A 5- or 6-alkoxycarbonyl-2,3-dicyanonaphthalene according to claim 1, which is 6-(n-octadecyloxycarbonyl)-2,3-dicyanonaphthalene.

6. A 5- or 6-alkoxycarbonyl-2,3-dicaynonaphthalene according to claim 1, which is 6-(n-tetradecyloxycarbonyl)-2,3-dicyanonaphthalene.

7. A 5- or 6-alkoxycarbonyl-2,3-dicyanonaphthalene according to claim 1, which is 6-(n-hexadecyloxycarbonyl)-2,3-dicyanonaphthalene.

8. A 5- or 6-alkoxycarbonyl-2,3-dicyanonaphthalene according to claim 1, which is 6-(n-eicosyloxycarbonyl)-2,3-dicyanonaphthalene.

9. A 5- or 6-alkoxycarbonyl-2,3-dicyanonaphthalene according to claim 1, which is 6-(n-docosyloxycarbonyl)-2,3-dicyanonaphthalene.

* * * * *